US007892181B2

(12) United States Patent
Christensen et al.

(10) Patent No.: US 7,892,181 B2
(45) Date of Patent: *Feb. 22, 2011

(54) APPARATUS FOR MONITORING INTRA-ABDOMINAL PRESSURE

(75) Inventors: Mark A. Christensen, Salt Lake City, UT (US); Timothy R. Wolfe, Salt Lake City, UT (US); Perry W. Croll, Salt Lake City, UT (US); Marshall T. Denton, Salt Lake City, UT (US); Edward J. Kimball, Salt Lake City, UT (US)

(73) Assignee: AbViser Medical LLC, Salt Lake City, UT (US)

( * ) Notice: Subject to any disclaimer, the term of this patent is extended or adjusted under 35 U.S.C. 154(b) by 409 days.

This patent is subject to a terminal disclaimer.

(21) Appl. No.: 11/219,319

(22) Filed: Sep. 1, 2005

(65) Prior Publication Data

US 2006/0058702 A1    Mar. 16, 2006

Related U.S. Application Data

(63) Continuation of application No. PCT/US2004/006409, filed on Mar. 1, 2004, which is a continuation-in-part of application No. 10/379,222, filed on Mar. 4, 2003, now Pat. No. 7,112,177.

(51) Int. Cl.
*A61B 5/00* (2006.01)
(52) U.S. Cl. ..................................................... 600/561
(58) Field of Classification Search ................ 600/561; 604/33, 77, 167.04, 167.03, 248, 339, 39, 604/45; 137/625.46, 45, 21
See application file for complete search history.

(56) References Cited

U.S. PATENT DOCUMENTS 1,600,793 A * 9/1926 Bogan .................... 137/625.45

(Continued)

FOREIGN PATENT DOCUMENTS

EP        0 258 690        8/1987

(Continued)

OTHER PUBLICATIONS

PCT International Search Report, PCT/US04/06409, dated Dec. 26, 2006.

(Continued)

*Primary Examiner*—Max Hindenburg
*Assistant Examiner*—Michael C Stout
(74) *Attorney, Agent, or Firm*—TraskBritt

(57) ABSTRACT

An improved apparatus for monitoring the intra-abdominal pressure of a hospitalized patient includes a urinary catheter connected to a urine valve having selectable communication positions between a discharge end of the urinary catheter and either a drain or a fluid source. Preferably, the urine valve has a housing adapted to resist patient discomfort from leg-valve contact. One operable protective housing may be embodied as a separate tray component. Plumbing structure desirably maintains fluid supply and drain conduits in a substantially parallel arrangement to assist routing those conduits between a patient's legs. When the urine valve is oriented for communication to the fluid source, an infusion pump may be used to introduce a known quantity of fluid through the urine valve and into the patient's bladder where the fluid's pressure can be measured. Desirably, a double check valve is included in a fluid supply path and arranged to permit repetitive operation of a syringe to inject a bolus of fluid into the patient's bladder. Subsequent to making a pressure measurement, the urine valve is returned to the bladder draining position.

22 Claims, 13 Drawing Sheets

U.S. PATENT DOCUMENTS

| | | | | |
|---|---|---|---|---|
| 1,666,332 | A * | 4/1928 | Hirsch | 73/747 |
| 1,712,848 | A | 5/1929 | Rose | |
| 2,417,994 | A | 3/1947 | Sheets | |
| 2,716,017 | A | 8/1955 | Linker | |
| 3,100,490 | A | 8/1963 | Desautels | |
| 3,103,229 | A | 9/1963 | Smith | |
| 3,620,255 | A | 11/1971 | Stillman | |
| 3,674,052 | A | 7/1972 | Hartman et al. | |
| 3,794,043 | A | 2/1974 | McGinnis | |
| 4,210,173 | A | 7/1980 | Choksi et al. | |
| 4,217,911 | A * | 8/1980 | Layton | 600/561 |
| 4,301,811 | A * | 11/1981 | Layton | 600/561 |
| 4,538,621 | A | 9/1985 | Jarczyn | |
| 4,705,073 | A * | 11/1987 | Beck | 137/625.25 |
| 4,966,161 | A | 10/1990 | Wallace et al. | |
| 5,064,165 | A | 11/1991 | Jerman | |
| 5,207,641 | A * | 5/1993 | Allton | 604/32 |
| 5,385,563 | A | 1/1995 | Gross | |
| 5,433,216 | A | 7/1995 | Sugrue et al. | |
| 5,540,668 | A * | 7/1996 | Wilson et al. | 604/248 |
| 5,647,845 | A | 7/1997 | Haber et al. | |
| 5,713,850 | A | 2/1998 | Heilmann et al. | |
| 5,865,764 | A | 2/1999 | Moorhead | |
| 5,899,434 | A | 5/1999 | Nishimura | |
| 5,916,153 | A | 6/1999 | Rhea | |
| 5,916,230 | A * | 6/1999 | Brenneman et al. | 606/172 |
| 6,102,888 | A | 8/2000 | Walker | |
| 6,287,265 | B1 * | 9/2001 | Gleason | 600/573 |
| 6,334,064 | B1 | 12/2001 | Fiddian-Green | |
| 6,382,001 | B1 * | 5/2002 | Neeley et al. | 70/175 |
| 6,434,418 | B1 | 8/2002 | Neal et al. | |
| 6,447,462 | B1 | 9/2002 | Wallace et al. | |
| 6,494,208 | B1 | 12/2002 | Morejon | |
| 6,503,208 | B1 * | 1/2003 | Skovlund | 600/561 |
| 6,645,183 | B2 | 11/2003 | Christensen | |
| 6,877,714 | B2 | 4/2005 | Hall | |
| 7,097,632 | B2 * | 8/2006 | Shia et al. | 604/77 |
| 7,112,177 | B2 | 9/2006 | Christensen et al. | |
| 7,240,740 | B2 | 7/2007 | Reilly et al. | |
| 7,381,190 | B2 | 6/2008 | Sugrue et al. | |
| 7,644,722 | B2 | 1/2010 | Christensen | |
| 7,726,328 | B2 | 6/2010 | Christensen et al. | |
| 2002/0065472 | A1 | 5/2002 | Brockway et al. | |
| 2002/0082610 | A1 | 6/2002 | Cioanta et al. | |
| 2002/0115966 | A1 | 8/2002 | Christensen et al. | |
| 2003/0062281 | A1 * | 4/2003 | Giard et al. | 206/364 |
| 2003/0195478 | A1 | 10/2003 | Russo | |
| 2004/0082909 | A1 * | 4/2004 | Shia et al. | 604/77 |
| 2006/0058702 | A1 | 3/2006 | Christensen et al. | |
| 2007/0255167 | A1 | 11/2007 | Christensen et al. | |
| 2008/0103408 | A1 | 5/2008 | Denton et al. | |
| 2008/0114316 | A1 | 5/2008 | Christensen et al. | |

FOREIGN PATENT DOCUMENTS

| | | |
|---|---|---|
| GB | 2123300 A | 2/1984 |
| JP | 9-72252 | 3/1997 |
| JP | 10-305104 | 11/1998 |
| JP | 11-503926 | 4/1999 |
| JP | 11-155821 | 6/1999 |
| JP | 11-263587 | 9/1999 |
| JP | 2002-360705 | 12/2002 |
| WO | WO 96/22118 | 7/1996 |
| WO | WO 98/42397 | 10/1998 |
| WO | WO 2004/078235 A2 | 9/2004 |
| WO | WO 2004/080519 A1 | 9/2004 |
| WO | WO 2006/060248 | 2/2007 |

OTHER PUBLICATIONS

PCT International Search Report, PCT/AU2004/000282, dated Apr. 28, 2004.

PCT Written Opinion, PCT/AU2004/000282, dated Apr. 28, 2004.

Fusco, Mark A., et al. "Estimation of Intra-abdominal Pressure by Bladder Pressure Measurement: Validity and Methodology," 50(2) The Journal of Trauma® Injury, Infection, and Critical Care 297302 (Feb. 2001).

Kirkpatrick, Andrew W., et al., "Is Clinical Examination an Accurate Indicator of Raised Intraabdominal Pressure in Critically Injured Patients?" 43(3) CJS 207-211 (Jun. 2000).

Lozen, Yvonne, "Intraabdominal Hypertension and Abdominal Compartment Syndrome in Trauma: Pathophysiology and Interventions," 10(1) AACN Clinical Issues: Advanced Practice in Acute Critical Care 104112 (Feb. 1999), http://gateway2.ovid.com/ovidweb.cgi (11 pages) Dec. 9, 2002.

Malbrain, M.L.N.G., "Abdominal pressure in the critically ill: measurement and clinical relevance," 25 Invensive Care Med. 1453-1458 (1999).

Sugrue, Michael, "Intra-abdominal pressure: time for clinical practice guidelines?" 28 Intensive Care Med. 389391 (2002).

U.S. Appl. No. 11/825,215, filed Jul. 3, 2007, Christensen et al., Apparatus for Monitoring Intra-Abdominal Pressure.

International Preliminary Report on Patentability, PCT/US2004/033463, dated Apr. 11, 2007.

Partial European Search Report for EP 04 79 4734 dated May 29, 2009.

Cheatham et al., Intraabdominal Pressure: A Revised Method for Measurement, 1997, pp. 594-95, Elsevier Science Inc.

Burch et al., Abstract, The abdominal compartment syndrome, Surg. Clin. North Am., 1996, pp. 833-842, vol. 76.

Kron et al., The measurement of intra-abdominal pressure as a criterion for abdominal re-exploration, Ann. Surg.. 1984, pp. 28-30, vol. 199.

Iberti et al., Abstract. A simple technique to accurately determine intra-abdominal pressure, Crit. Care Med., 1987, pp. 1140-1142, vol. 15.

Iberti et al., Abstract, Determination of intra-abdominal pressure using a transurethral bladder catheter: clinical validation of the technique, Anesthesiology, 1989, pp. 47-50, vol. 70.

Platt et al., Abstract, Mortality associated with nosocomial urinary-tract infection. N. Eng. J. Med.. 1982. pp. 637-642. vol. 307.

Office Action for U.S. Appl. No. 11/825,215, dated Dec. 16, 2008.

Office Action for U.S. Appl. No. 11/825,215, dated Sep. 28, 2009.

U.S. Appl. No. 12/583,823, filed Aug. 26, 2009, Christensen et al., Medical Valve and Method to Monitor Intra-Abdominal Pressure.

Supplementary Partial European Search Report for EP 04 79 4734 dated May 29, 2009.

* cited by examiner

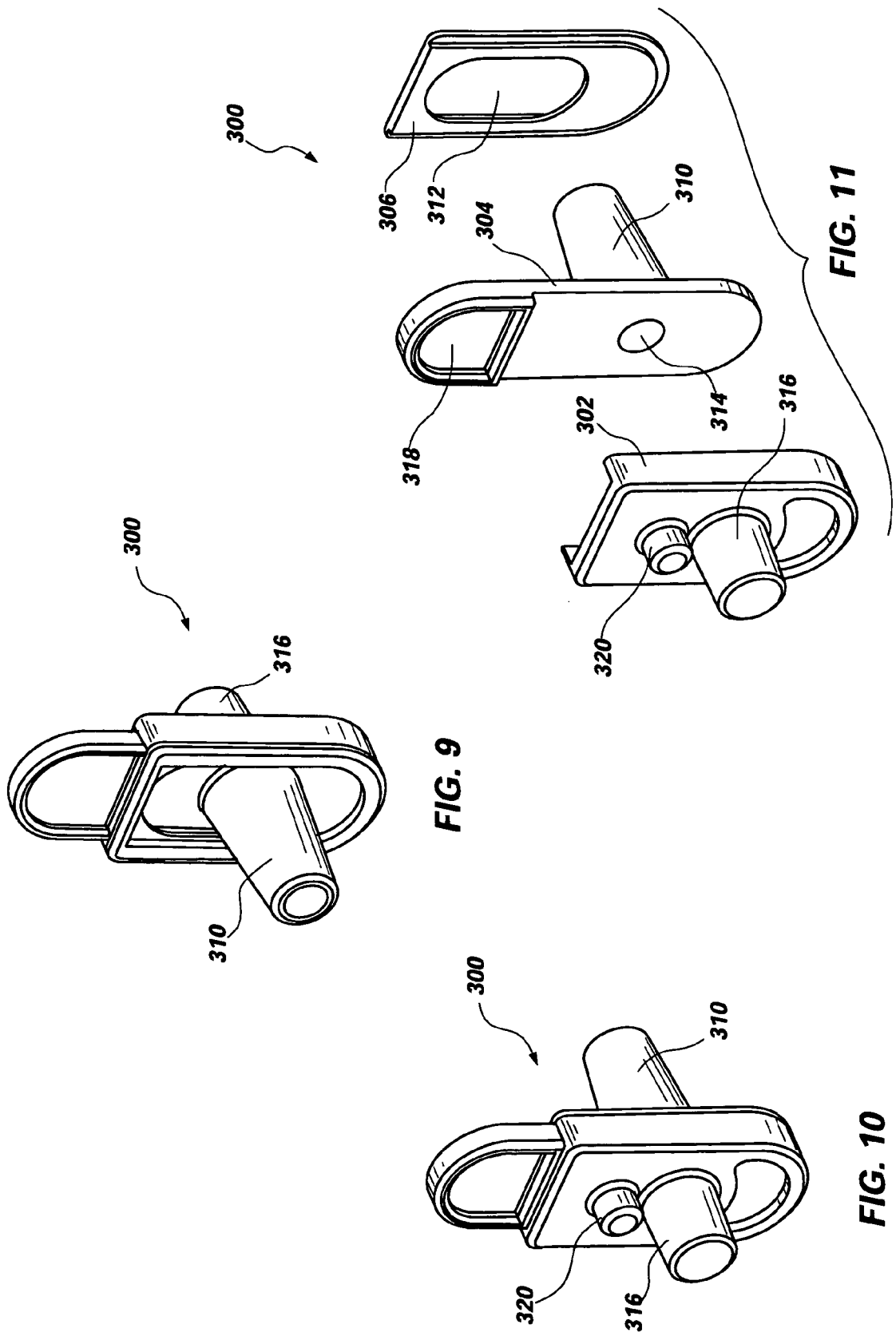

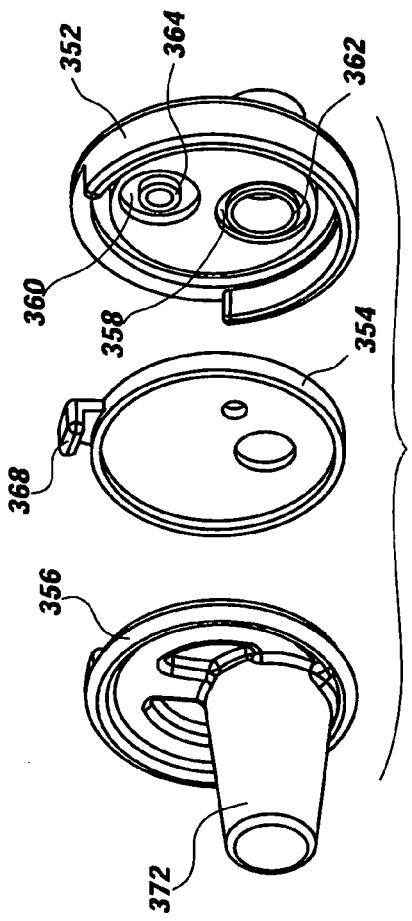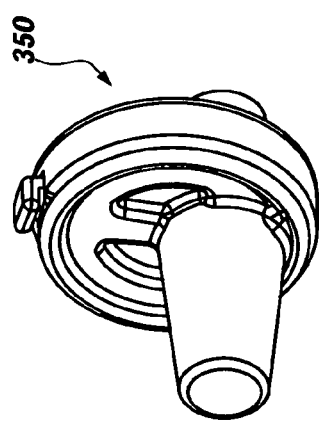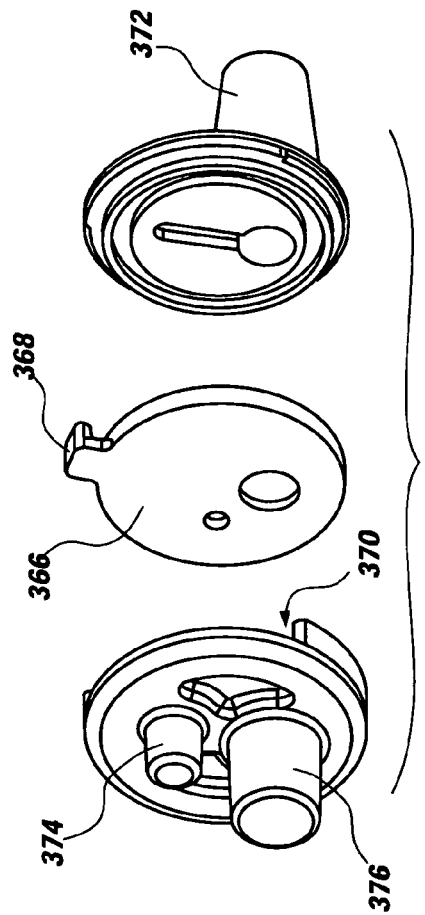

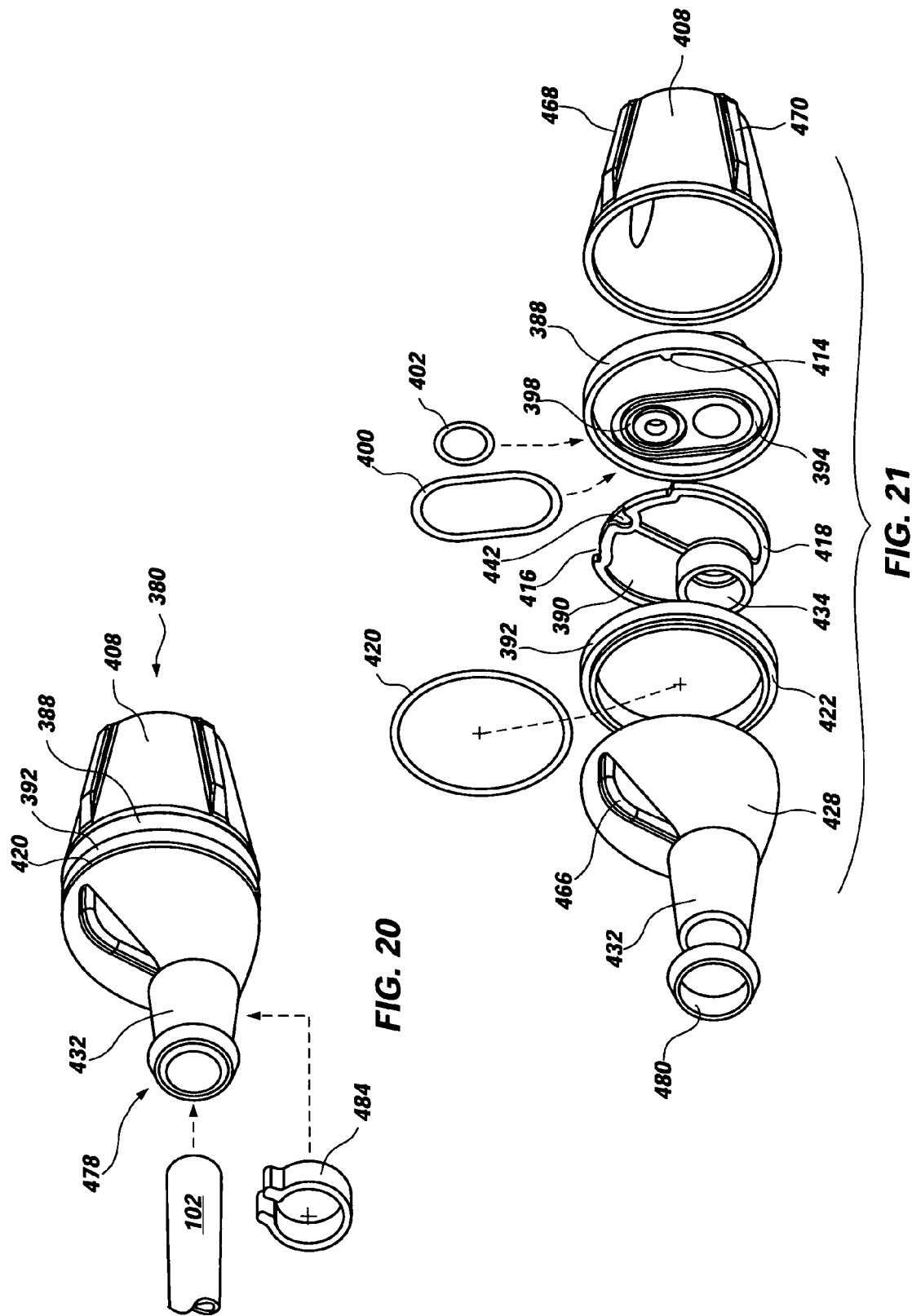

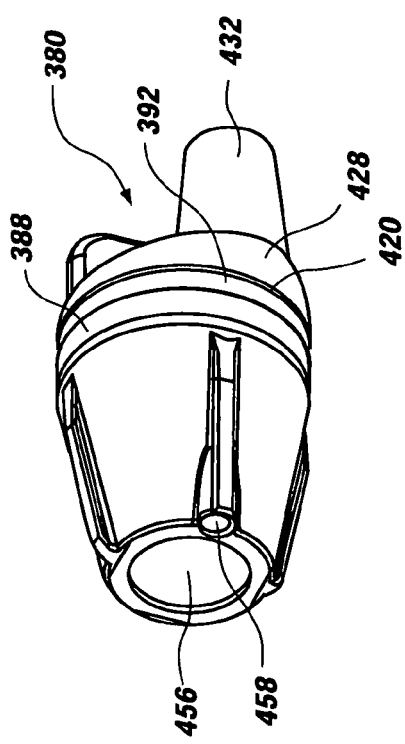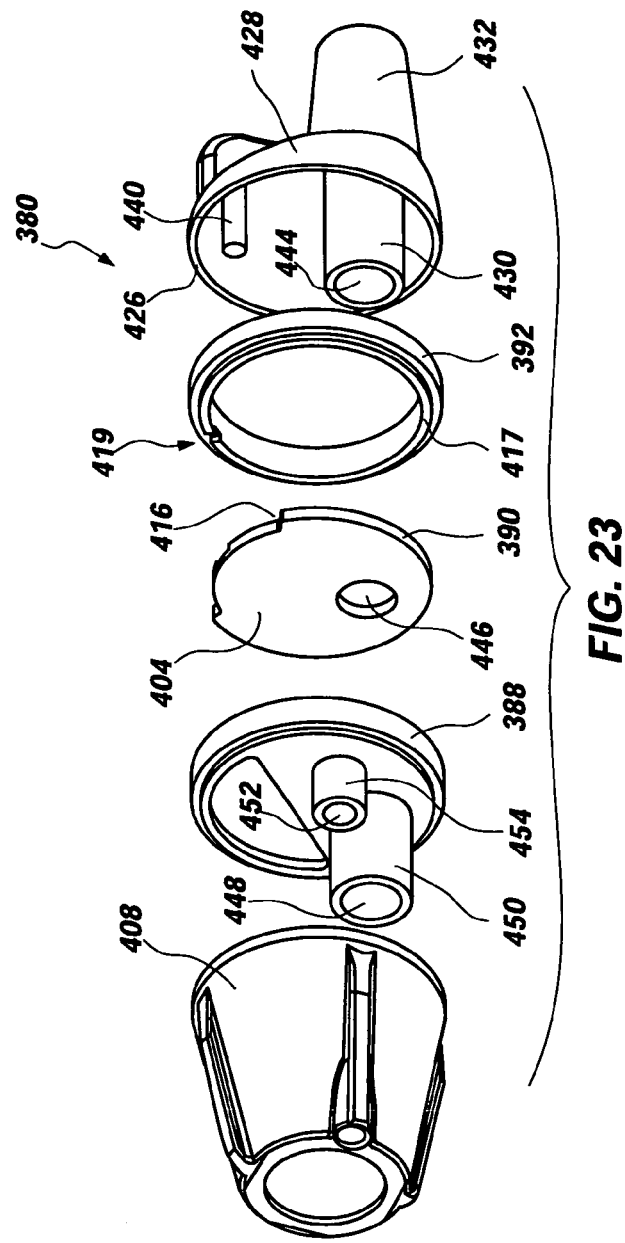

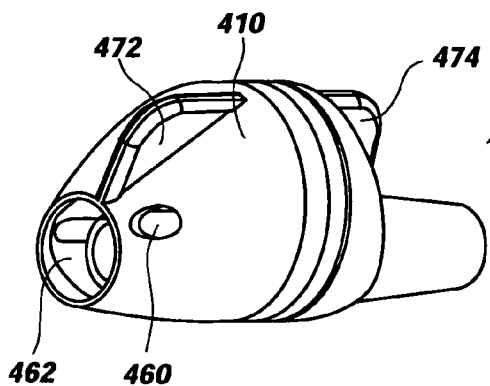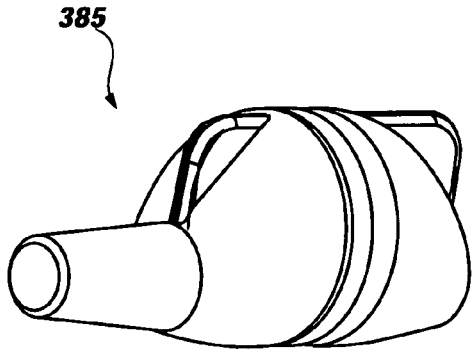
FIG. 26　　　　　　　　　　　FIG. 24
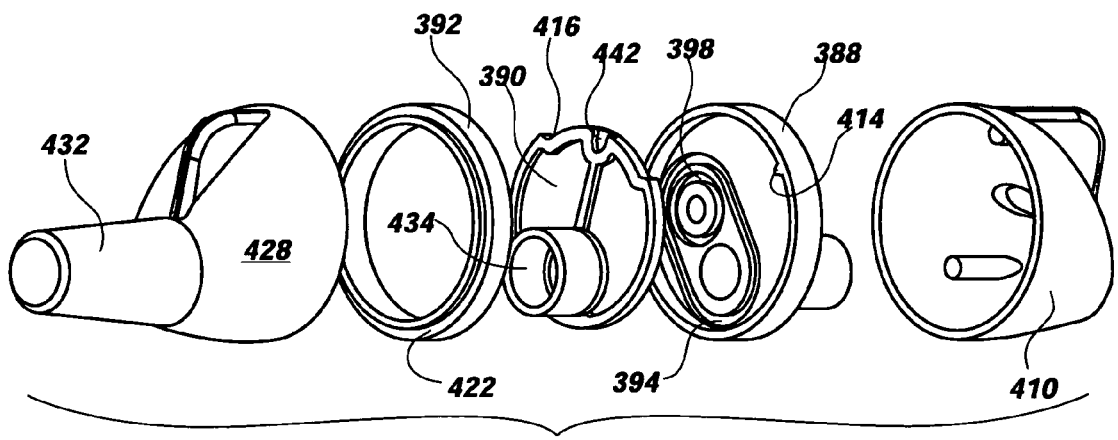
FIG. 25
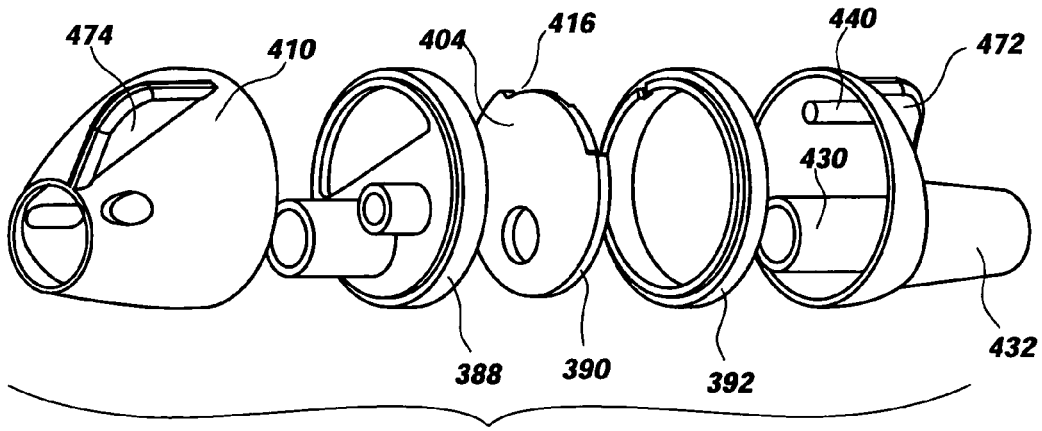
FIG. 27

APPARATUS FOR MONITORING INTRA-ABDOMINAL PRESSURE

CROSS-REFERENCE TO RELATED APPLICATIONS

This application is a continuation of PCT International Patent Application No. PCT/US2004/006409, filed on Mar. 1, 2004, designating the United States of America, and published, in English, as PCT International Publication No. WO 2004/078235 A2 on Sep. 16, 2004, which application is a continuation in part of U.S. patent application Ser. No. 10/379,222, filed Mar. 4, 2003, for "APPARATUS FOR MONITORING INTRA-ABDOMINAL PRESSURE," pending, the contents of both of which are incorporated by this reference.

TECHNICAL FIELD

The invention relates generally to plumbing devices including valves and conduits, and to pressure measurement equipment. The invention relates particularly to apparatus configured as an assembly to infer intra-abdominal pressure of a medical patient by measuring bladder pressure.

BACKGROUND

Elevated intra-abdominal pressure leads to major changes in the body's physiology that, if undetected and untreated, can result in organ damage and patient death. When patients become critically ill, they may develop a capillary leak phenomenon that causes the tissues in their body to become edematous with extra fluid that seeps out of the capillaries. This process is called "3rd spacing" of fluid. It is very common in sepsis, burn, trauma and post-operative patients. One area of the body where 3rd spacing is especially prevalent is the abdominal cavity. Critically ill patients can have many liters of fluid leak into the intestinal wall, the intestinal mesentery, and the abdominal cavity (as free fluid sloshing around the intestines).

Fluid 3rd spacing in the abdominal cavity results in an increase in intra-abdominal pressure (IAP). Normal IAP is 0 mmHg to subatmospheric (less than 0). Once the pressure builds to 12-15 mmHg, intra-abdominal hypertension (IAH) occurs. At this point, methods to improve intestinal perfusion should be started, such as: fluid loading to increase blood flow to gut, inotropic support to increase cardiac output, etc. As pressures increase above 20-25 mmHg, the abdominal compartment syndrome (ACS) exists and major physiologic and organ system dysfunction result. Decompressive surgery (vertical midline abdominal incision) is often required to prevent irreversible organ damage and death. The exact pressure at which abdominal decompression should occur is dependent on a number of host factors including age, underlying co-morbidities and physiologic evidence of developing ACS.

Early detection of increasing abdominal pressure allows the clinician to intervene before irreversible organ damage occurs and may be life saving. The only reliable method for early detection of increasing IAP is to place a catheter within a space in the abdomen (peritoneal cavity, stomach, bladder, rectum) and measure the pressure. The most commonly used method is to monitor bladder pressure through an indwelling Foley catheter. To monitor bladder pressure, clinicians are currently building their own devices out of many separate materials and inserting them into the Foley catheter.

Currently employed techniques used to monitor a patient's IAP are adapted to measure the pressure of fluid contained within the patient's bladder at intervals spaced apart in time. While the pressure reading at a pressure transducer may not correspond to the actual value of IAP (e.g. if the transducer is located at a different elevation than the bladder), trends in measured pressure will correlate to trends in IAP in the patient.

One way to measure a patient's IAP involves disassembling a urinary catheter drain tube to inject saline through the catheter and into the patient's bladder. (For convenience, a urinary catheter will generally be referred to in this disclosure as a Foley catheter, due to its common use.) Unfortunately, opening the closed drainage system plumbing places both the patient and the health practitioner at increased risk of infection. It is possible to use a three-way Foley catheter, but such catheters are more expensive and are not routinely used. Use of a three-way Foley catheter would require either preknowledge of its necessity, or replacement of a standard catheter. The former option increases costs, and the latter would increase both costs and risk of patient infection.

A different approach for introducing a bolus of fluid into a patient's bladder incorporates the aspiration port included in a urinary catheter drain system as a fluid injection port. The drain tube connected to the Foley catheter is blocked, and the needle of a syringe is passed through the drain tube's aspiration port to permit injection of a saline bolus. A manometer or pressure transducer is then connected to the needle to record bladder pressure. Undesirably, approaches involving use of needles, particularly in the vicinity of the patient's legs to assemble the pressure measuring apparatus, place both the patient and the health practitioner at risk of needle sticks.

With reference to FIG. 1, a currently preferred arrangement adapted to monitor a medical patient's IAP is generally indicated at 100. A patient is fitted with a urinary catheter 102, such as a Foley catheter. A fluid source, such as saline bag 104, is connected in fluid communication to the catheter 102 upstream of an occluding device 108 temporarily applied to block the catheter drain conduit 106. Interruption of the urine drain path from the patient generally is permitted only temporarily as required to effect pressure measurements.

The device 100 includes a pair of two-way or three-way stopcocks, 110 and 112, respectively. One end of fluid supply tube 114 is connected to a one liter saline bag 104. The other end of fluid supply tube 114 is connected to an inlet port of stopcock 110. A valve stem in stopcock 110 may be oriented to permit fluid to flow from bag 104 toward syringe 116. When syringe 116 is full, or charged with fluid as desired, the valve stem of stopcock 110 is adjusted by way of a manual rotation to permit fluid flow from the syringe toward stopcock 112 while resisting fluid flow toward bag 104. Stopcock 112 can be adjusted to direct a bolus of fluid from syringe 116 for flow through tubing 120 towards catheter 102. Stopcock 112 may also be adjusted to an alternate configuration to provide fluid communication between a pressure measuring device 121 and tubing section 120 while resisting fluid flow toward stopcock 110. An infusion needle or angiocatheter 122 carried at an end of tubing 120 is inserted into urine collection port 125 to couple the tube 120 in fluid communication to the catheter 102.

The steps typically required to measure a patient's LAP, using the arrangement of FIG. 1, are as follows: First the apparatus 100 is assembled, including inserting the needle of an angiocatheter 122 into aspiration port 125 connected to a Foley catheter 102 installed in a patient. Stopcock 110 is oriented to permit fluid flow between bag 104 and syringe 116, and the syringe is filled with saline. Stopcocks 110 and 112 are then both adjusted for fluid flow from the syringe 116 toward the catheter 102. Tube 120 is flushed and filled with saline. Then tubing 106 is occluded to resist fluid flow in a drain direction from catheter 102. Typically, stopcock 112 is then adjusted to resist fluid flow toward syringe 116 and stopcock 110 is configured to permit fluid flow between bag 104 and syringe 116 so that the syringe 116 can be refilled with saline. After priming syringe 116, stopcock 110 and 112 are adjusted for fluid flow between syringe 116 and catheter 102 to place a bolus of fluid into the patient's bladder. Then, stopcock 112 is oriented to provide fluid communication between conduit 120 and pressure transducer 121 while resisting fluid flow toward stopcock 110. Pressure apparatus 121 then indicates the current pressure in the patient's bladder, which may be correlated to IAP. Subsequent to making and recording the pressure measurement, the occlusion of drain 106 is removed to permit draining the bolus of fluid from the patient's bladder. Such procedure is repeated at intervals spaced apart in time to record trends in the patient's IAP. The bolus of injected fluid desirably is less than about 100 mL and of uniform size during each successive pressure measurement to avoid effect from bladder wall musculature.

Occluding device 108 may be a clamp or hemostat as illustrated, or sometimes may be a valve. However, operable medical grade valves that are commercially available, such as two-way or three-way stopcocks 110 and 112, typically introduce undesired complications. One complication is that the available medical grade stopcocks typically provide drainage passageways that are too small in diameter for use in a urinary catheter drain. Clogging of the urine drain bore would be a serious problem.

The location of a catheter drain-occluding valve for a pressure measurement system desirably is in close proximity to the catheter 102—therefore between the patient's legs. Another complication substantially precluding direct inclusion of available medical grade two-way or three-way valves or stopcocks is that such devices route fluid conduits in orthogonal directions at the valve connection locations, thereby creating protruding and invasive plumbing that is uncomfortable to the patient. Furthermore, currently available valves and stopcocks also have protrusions (such as valve actuators or handles), and sharp corners or abrupt changes in shape, that place a patient at risk of injury should such protrusion or corner be impressed into a patient's skin.

The procedures for measuring trends in a patient's IAP described above undesirably place a patient at risk of infection, or require tiresome manual adjusting of a plurality of plumbing devices, such as two-way valves or stopcocks. It would be a desirable improvement to provide a device for measuring trends in a patient's IAP that is faster and more simple to operate. It would be a further advance to eliminate operations requiring needles to assemble or use the pressure measurement apparatus. A still further advance in the art would enhance the patient's comfort and increase the patient's protection from injury by resisting contact between the patient and uncomfortable or even harmful medical apparatus.

SUMMARY OF THE INVENTION

An apparatus and method for measuring hydraulic pressure in the bladder of a medical patient to infer intra-abdominal pressure (IAP). The apparatus may be embodied to include a catheter adapted for draining urine from a patient, a container of fluid, a fluid pump disposed to urge fluid flow from the container toward the patient's bladder, a pressure transducer arranged to measure a pressure of fluid in the bladder, and an automatic flow-control device. One operable automatic flow control device is actuated by fluid pressure effected by the pump. Preferred flow-control devices are operable to permit flow of fluid from the container toward the pump and to resist flow of fluid from the pump back toward the container. The flow-control device desirably also permits flow of fluid in a direction from the pump toward the catheter and resists flow of the fluid in a direction from the pressure transducer toward the pump. A flow-control device may be embodied as a double check valve, or as a check-bypass valve functional as a double check valve. Operable pumps include medical infusion pumps in general. One currently preferred pump is a syringe disposed to effect a cyclic fluid pressure at a staging area between first and second operable check valve portions of the double check valve. Commonly, a valve arrangement operable as a double check valve is attached to a discharge end of the syringe. The combination of the double check valve and a syringe enhances speed at which the IAP measurement can be performed.

A urine valve desirably is included in the IAP apparatus to further facilitate making a pressure measurement. One operable urine valve typically is arranged to provide a first flow portion disposed in a first fluid path from the container of fluid, a second flow portion disposed in a second fluid path operable as a drain for fluid received from the catheter and discharged through the urine valve; and a third flow portion disposed for fluid communication with a urine discharge end of the catheter. To speed up the IAP measurement, a urine valve may be operable selectively to resist fluid flow between the third flow portion and the second flow portion. Such a urine valve further is operable selectively to resist fluid flow between the first flow portion and the third flow portion.

A urine valve may be shaped to assist in routing of fluid conduits in the space between a patient's legs. Desirably, the first and second flow portions of the urine valve provide structure configured to permit connection to respective first and second substantially parallel conduits to facilitate routing those conduits between a patient's legs. It is further desirable for first, second, and third flow portions of the urine valve to include structure adapted for connection to substantially parallel conduit sections to streamline the fluid conduit plumbing arrangement. Sometimes, alternative connection structure is provided in fluid communication with each of the first, second, and third flow portions of the urine valve for connection to first, second, and third substantially parallel conduits, to facilitate routing those substantially parallel conduits in a space between a patient's legs. Connection structure within contemplation includes angle fittings.

Urine valves of different construction may be actuated in many ways to select a flow path through the valve. In a preferred embodiment, a flow path through the urine valve is selected by rotating a first valve structure with respect to a second valve structure. The operable fluid flow path can be selected by rotating a first portion of a valve housing with respect to a second portion of the housing. In the latter arrangement, first and second portions of the housing typically are sealed against infiltration by external contaminants.

Desirably, structure carried on the housing of a urine valve is adapted to provide visual indication of a currently selected flow path. Operable structure to provide a visual valve-position indication includes aligning wing-like protrusions, and colored bands. In one preferred embodiment, a colored marker band is aligned with a signal band of a like color when the valve is positioned for urine-draining, and the marker band is aligned with a signal band of a distinctly dissimilar color when the valve is placed in a pressure recording position. Certain preferred urine valves may include mechanical lockout structure that is engagable only when the valve is oriented to a urine draining position. The lockout structure provides an additional procedural step to ensure the valve is returned to draining mode subsequent to each pressure test on the patient.

One currently preferred urine valve includes first and second apertures, opening to portions of respective first and second flow paths through the valve, that are disposed on a first surface. A valve core element includes a second surface structured in cooperation with the first surface such that a third aperture disposed on the second surface can be aligned to form a leak resistant seal for fluid communication with either of the first and second apertures. The third aperture may be characterized as opening to a portion of a flow path in common to the first and second flow paths. The first and second surfaces can be flat, or planar, or may be curved in various directions. In a preferred embodiment of a urine valve, the leak resistant seal includes first and second O-rings. In that embodiment, the first O-ring is disposed on the first surface and arranged to encompass the first aperture. The second O-ring is disposed on the first surface and arranged to encompass the first aperture and the second aperture.

A second preferred urine valve is structured to provide flow portions arrange in general accordance with the aforementioned urine valve. A urine draining bore, formed by first and third flow paths through the valve, typically is sized in substantial agreement with a diameter of a urine draining catheter to resist its occlusion from contaminants carried in a urine stream. The urine valve body desirably is sized substantially as small as practical in diameter to facilitate placement of the valve between a patient's legs and to avoid imparting contact-induced discomfort to that patient. A leak resistant seal disposed about first and second apertures may be formed by a B-shaped O-ring. A third aperture, carried on a core element, can be aligned for selective and leak-resistant fluid communication with either of the first and second apertures. Of course, separate O-ring seals having a conventional round shape, and individually disposed radially around the first and second apertures, are also within contemplation in alternative valve embodiments.

Commonly, a body of a urine valve includes a housing structured to resist imparting contact injury to a patient. Desirably, a urine valve body is structured to provide a blunt contact at a patient interface location. It is further desirable for a protective housing to include smooth surfaces and rounded corners to resist formation of crevices in which contaminants might be shielded, to facilitate cleaning fecal matter, or other patient excretions, from an exterior surface of the housing.

A protective tray may be provided as an alternative, or in addition, to a protective valve housing. Such a tray is operable as a protective housing and generally includes blunt corners and areas of gradual transition in curvature to resist injury to a patient arising from contact to the tray. The tray typically defines a socket operable to space structure received in the socket apart from a patient. For example, a socket may be structured to receive a urine valve. The socket may further accommodate a discharge end portion of structure associated with the catheter. Certain sockets are adapted to hold the discharge end portion of a catheter in a preferred orientation to assist a health practitioner in inserting a needle into the catheter's aspiration port.

An alternative embodiment of an IAP apparatus may include a catheter adapted for draining urine from the patient, a container of fluid, a fluid pump, a pressure transducer arranged to measure a pressure of the fluid at a location downstream of the pump, and a multi-way urine valve. The multi-way urine valve includes first, second and third flow portions. The first flow portion of the valve is disposed in a first fluid path arranged to transfer fluid from the container to the catheter. The second flow portion is disposed in a second fluid path configured as a drain for the catheter. The third flow portion is disposed in the first fluid path for fluid communication between the valve and a discharge end of the catheter. In use, the multi-way valve is operable selectively to resist fluid flow between at least the third flow portion and the second flow portion. Desirably, a urine draining lumen forming a flow path through the valve has a diameter in excess of about 3/16 inches (4.8 mm) to resist occlusion from a build-up of matter discharged from the patient's bladder. Furthermore, a sealing element of the multi-way valve is desirably structured to contain a dead volume of less than about 0.001 cubic inches (16 ml) to reduce contaminant containment, to resist infection transmittal.

The IAP measurement procedure can be performed manually, or with an automated system. Certain embodiments of the invention can incorporate automated fluid pumping and valve actuation operable to record IAP at programmed intervals of time without requiring human intervention. Pressure measurements can be displayed at local and/or remote locations. Therefore, a health practitioner can remain at a remote central location and monitor the vital statistics, including IAP, of a plurality of patients.

A method for measuring hydrostatic pressure in the bladder of a medical patient typically includes the steps of: a) installing a urinary catheter to provide fluid communication on a first fluid path between the bladder and a discharge portion of the catheter; b) affixing a urine valve (having drain and measure orientations) to the catheter; c) connecting a source of fluid to a pump operable to urge the fluid toward the catheter; d) disposing a pressure transducer between the pump and bladder to measure the fluid's pressure; e) placing the urine valve into the measure orientation and operating the pump to introduce a bolus of the fluid into the bladder; f) using the pressure transducer to measure a hydrostatic pressure of the fluid; and g) placing the urine valve into the drain orientation to empty the bladder. Usually, steps e) through g) are repeated in sequence as an IAP measurement procedure performed a plurality of instances that are spaced apart in time. Desirably, operation of the pump in step e) entails actuation of a syringe to cause cyclic pressure fluctuation at a staging area of an automatic valve arrangement operable to permit fluid flow from the fluid source toward the catheter and to resist fluid flow in a reverse direction.

BRIEF DESCRIPTION OF DRAWINGS

In the drawings, which illustrate what are currently considered to be the best modes for carrying out the invention:

FIG. 9 is a view in perspective from a proximal end of a first urine valve;

FIG. 10 is a view in perspective from a distal end of the urine valve illustrated in FIG. 9;

FIG. 11 is an exploded view in perspective of the urine valve illustrated in FIG. 10;

FIG. 16 is a view in perspective from a proximal end of a third urine valve;

FIG. 17 is an exploded view in perspective of the urine valve illustrated in FIG. 16;

FIG. 18 is a view in perspective from a distal end of the third urine valve;

FIG. 19 is an exploded view in perspective of the urine valve illustrated in FIG. 18;

FIG. 20 is a view in perspective from a proximal end of a fourth urine valve;

FIG. 21 is an exploded view in perspective of the urine valve illustrated in FIG. 20;

FIG. 22 is a view in perspective from a distal end of the fourth urine valve, but with the hose barb removed;

FIG. 23 is an exploded view in perspective of the urine valve illustrated in FIG. 22;

FIG. 24 is a view in perspective from a proximal end of a fifth urine valve;

FIG. 25 is an exploded view in perspective of the urine valve illustrated in FIG. 24;

FIG. 26 is a view in perspective from a distal end of the fifth urine valve;

FIG. 27 is an exploded view in perspective of the urine valve illustrated in FIG. 26;

DETAILED DESCRIPTION OF THE INVENTION

Figure 2:
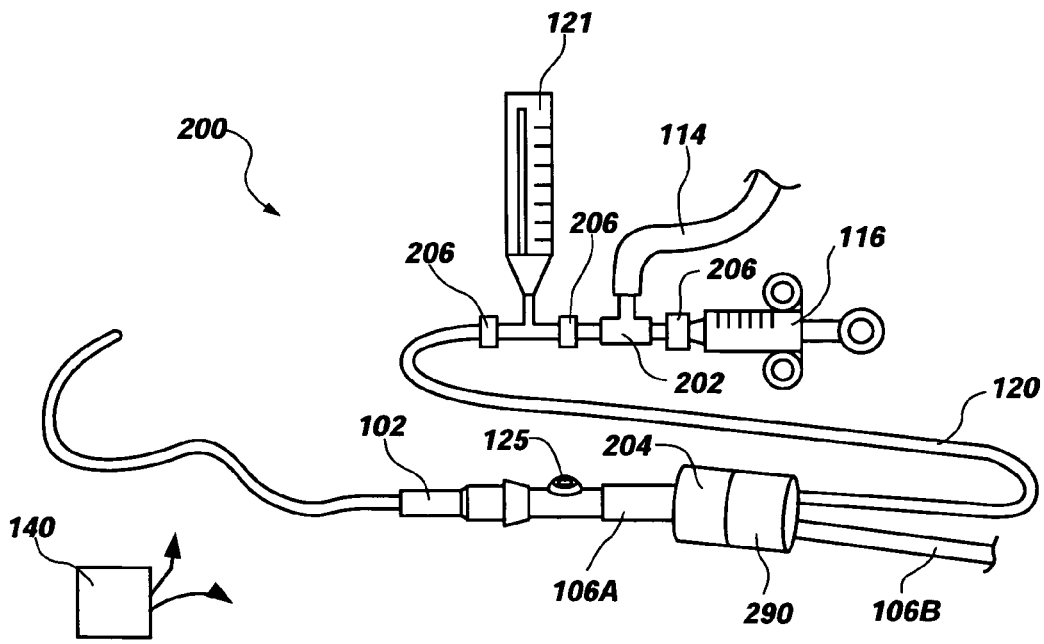
FIG. 2 illustrates a first currently preferred assembly for measuring a patient's bladder pressure.

FIG. 2 illustrates one currently preferred embodiment, generally indicated at 200, of an apparatus for measuring trends in a patient's intra-abdominal pressure. The assembly 200 includes a conduit 114 with one end in fluid communication with a saline or other fluid source (not illustrated). Conduit 114 desirably is connected at a second end for fluid communication with an automatic, direction-of-flow control device 202 to urge fluid flow through conduit 120 in a direction toward a patient. A hydraulic pressure in conduit 120 is measured by a pressure transducer, such as transducer 121.

Figure 1:
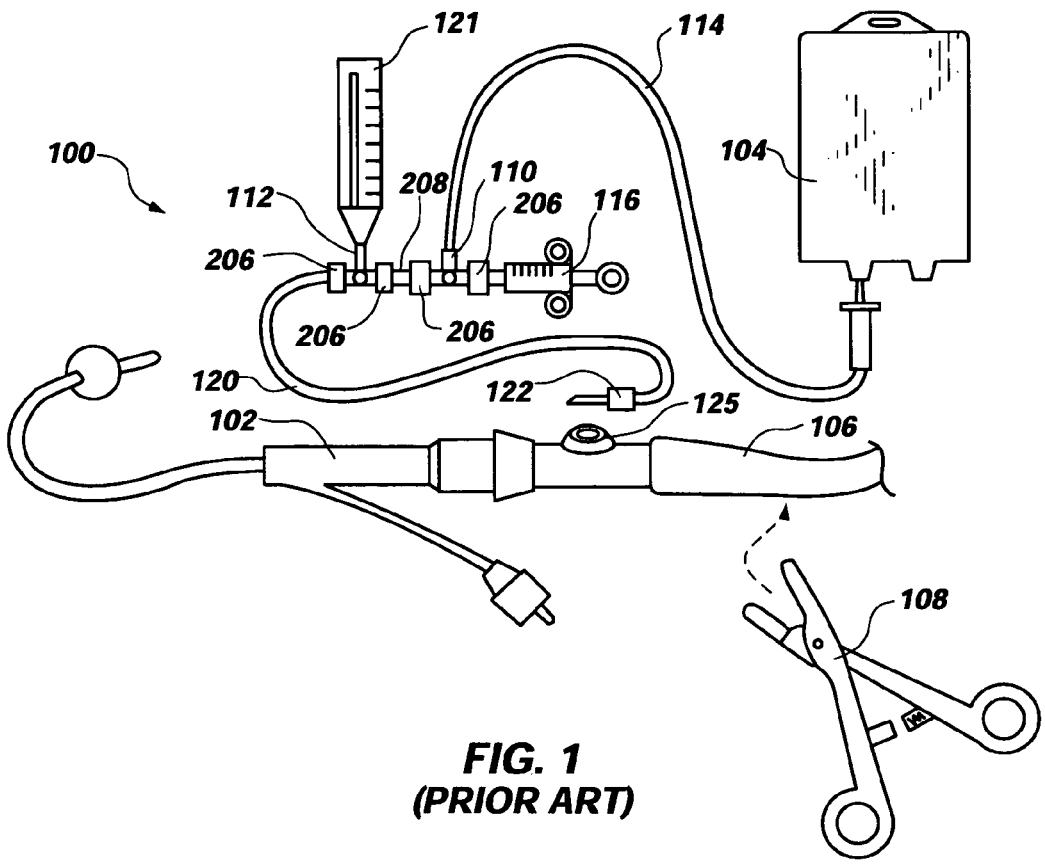
FIG. 1 illustrates a prior art assembly operable to measure a patient's bladder pressure.

It is actually preferred now to arrange the pressure transducer in a dead-ended conduit, compared to the flow-through arrangements illustrated in FIGS. 1 and 2. The preferred arrangement requires a clinician to make only one attachment at the pressure transducer area. In fact, one preferred embodiment of the invention is provided as a substantially preassembled kit in a package 140. The kit reduces chance of error by simplifying assembly of an IAP apparatus and reducing the number of decisions a clinician must make. Such a kit requires a clinician only to make a first connection to a saline bag 104, a second connection to a pressure transducer, and a third connection between an indwelling catheter and a urine drain container. Package 140 desirably is made from a material operable to maintain sterility of the assembled components included in the kit as the kit is transported and stored prior to use.

Flow control device 202 can generally be characterized as being cyclically operable with a staging infusion pump, such as syringe 116, to permit fluid flow from a fluid source during a filling stroke, and to resist fluid flow towards the fluid source during an expelling stroke, of the staging pump. Typically, one or more seal members carried inside of device 202 is/are biased for automatic operation to control a direction of fluid flow through the device 202. Therefore, a health practitioner is relieved of the tedious chore of adjusting the valve 202 manually to control a direction of fluid flow between cycles of an infusion pump such as syringe 116. Devices within contemplation for use as a flow control device 202 include a pair or more of check valves, a double check valve, and a check-bypass valve. Inclusion of an automatically actuated flow-control device 202 constitutes a first improvement over prior art assemblies.

As illustrated in FIG. 2, assembly 200 may optionally include a two-way valve 204 connected in fluid communication with a discharge port from flow control device 202. Two-way valve 204 may sometimes also be referred to in this disclosure as a type of urine valve, or a urine discharge or drain valve. For purposes of the invention, a two-way valve places a first conduit into selective fluid communication with either one, or the other, of two additional conduits. A three-way valve would also be operable, but there is not much need for a fluid supply port to communicate directly with a drain port in application of the instant invention. Valve 204 desirably is located in close proximity to a discharge of a Foley catheter 102 installed in a patient. A Foley catheter is not required, per se.—virtually any sort of urine draining catheter may be used.

As illustrated in FIG. 2, valve 204 is connected in fluid communication to Foley catheter 102 by way of a relatively short section of urine drain conduit 106A. Such close proximity to a discharge of catheter 102 reduces a volume of fluid required to be pumped through the system to effect a pressure measurement, and also helps to maintain the apparatus 200 in a tidy, organized arrangement. Inclusion of a two-way valve, such as valve 204, to selectively block a discharge from the catheter 102 simplifies operation of the assembly 200 compared to the prior art, and constitutes a second improvement providing several advantages.

Of course, a valve 204 may be adapted to connect directly to the discharge end of a urinary catheter without an intervening conduit section 106A. It is within contemplation for a valve 204 to carry structure adapted for connection directly to structure provided at a discharge area of a catheter. In general, connections between the various components forming an assembly 200 may be made as a matter of convenience, and using any operable type of plumbing connection joint.

In the embodiment illustrated in FIG. 2, valve 202 is connected to a discharge end of syringe 116 through a luer-locking type of joint 206. An alternative connection between any of the components in an IAP measuring assembly according to the invention, such as assembly 200, may include any operable fluid-tight connection formable between the components.

Stretches between components may also include intermediate structure, such as one or more sections of tubing 208 (see FIG. 1). Furthermore, the assembly 200 desirably is configured for arrangement its various components in convenient locations. For example, bag 104 typically is suspended from an elevated hanger, but pressure indicating manometer 121, or more specifically, its transducer portion, desirably is located at approximately the same elevation as the patient's bladder to reflect an equivalent pressure.

With reference still to FIG. 2, preferred embodiments of a two-way valve 204 provide connections for fluid supply conduit 120 and urine drain conduit 106B to place such conduits approximately in parallel. A substantially parallel arrangement of conduits 120 and 106B near the valve 204 increases patient comfort and also helps to maintain a tidy arrangement of assembly 200. Furthermore, the illustrated substantially in-line arrangement between conduits 106A and conduits 120 and 106B aides in routing the conduits in a path to minimize their intrusiveness to a patient.

Figure 3:
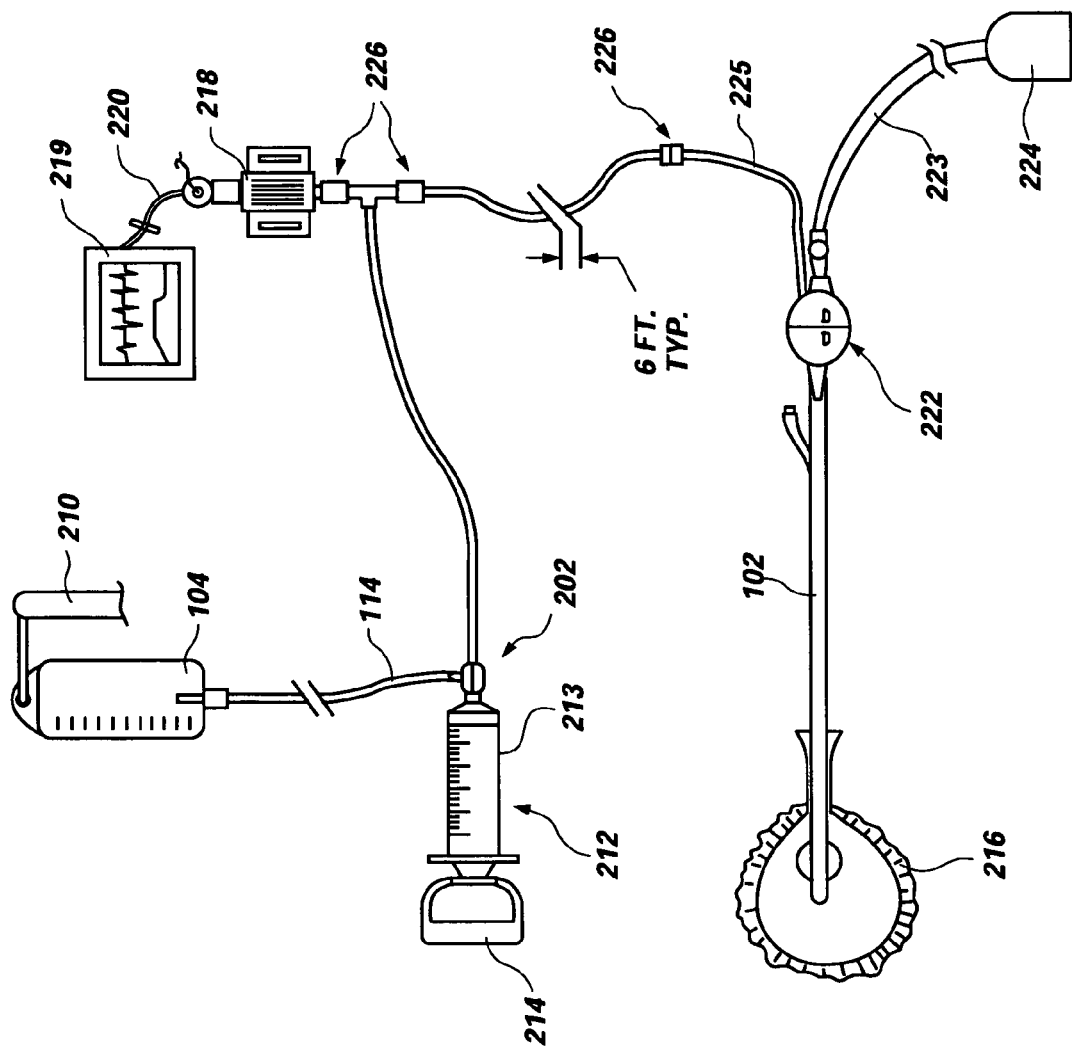
FIG. 3 illustrates a first currently preferred arrangement of equipment for measuring a patient's bladder pressure that locates a pressure transducer remote from the patient, and is depicted in urine drain mode.

FIG. 3 illustrates an arrangement of equipment for measuring IAP in a patient that locates most of the equipment at a convenient location remote from the patient. While equipment can be located at any convenient distance from the patient, it is generally located within a radius of about six to ten feet, or so. The IAP measurement equipment desirably is assembled using a procedure operable to resist degrading sterility of the catheter draining system.

In the illustration of FIG. 3, apparatus including the saline fluid source 104 can be suspended from equipment stands, such as stand 210. Fluid flow control device 202 and syringe 212 may be located in convenient proximity to the saline bag 104. Illustrated syringe 212 is representative of a larger model, perhaps having a volume capacity of 50 ccs. Such a syringe 212 typically is operated using both hands. An operator grasps the syringe barrel 213 with one hand and actuates the plunger held in the palm of the other hand at transverse handle 214. Cyclic actuation of the syringe 212 automatically operates the fluid flow control device 202 to urge fluid flow in the direction toward the patient's bladder 216.

Pressure transducer 218 desirably is suspended from some structure at an elevation substantially in correspondence with the patient's bladder. Transducer 218 can be affixed to a wall, stand 210, a side of the patient's bed, or any other convenient location. Pressure display terminal 219 can be placed for convenient monitoring by a health practitioner. Electric cable 220 communicates the pressure signal from the transducer 218 to the display device 219.

Desirably, a large portion of an IAP measuring apparatus is provided in a preassembled form, e.g. as a kit, to reduce decision making required of clinicians. One exemplary such kit simply requires connection of a kit's fluid supply conduit to a fluid source, such as a saline bag; connection of a pressure transducer to the kit's measurement conduit; and connection of the kit's urine valve between an indwelling catheter and drain container.

The urine discharge valve illustrated in FIG. 3, and generally indicated at 222, is shown in a configuration for discharge of urine through urine catheter 102 placed into fluid communication with the patient's bladder 216. Valve 222 is normally placed into the position illustrated, so that urine drains through valve 222, through drain conduit 223, and into urine bag 224. Some valves 222 may include one or more sections of conduit, such as drain conduit 223 and/or fluid supply conduit 225 permanently affixed by known manufacturing methods to the body of the valve 222. In such case, a connector, such as the luer-locking type connector generally indicated at 226, may be provided to facilitate making plumbing connections in the intra-abdominal pressure monitoring apparatus assembly.

Figure 4:
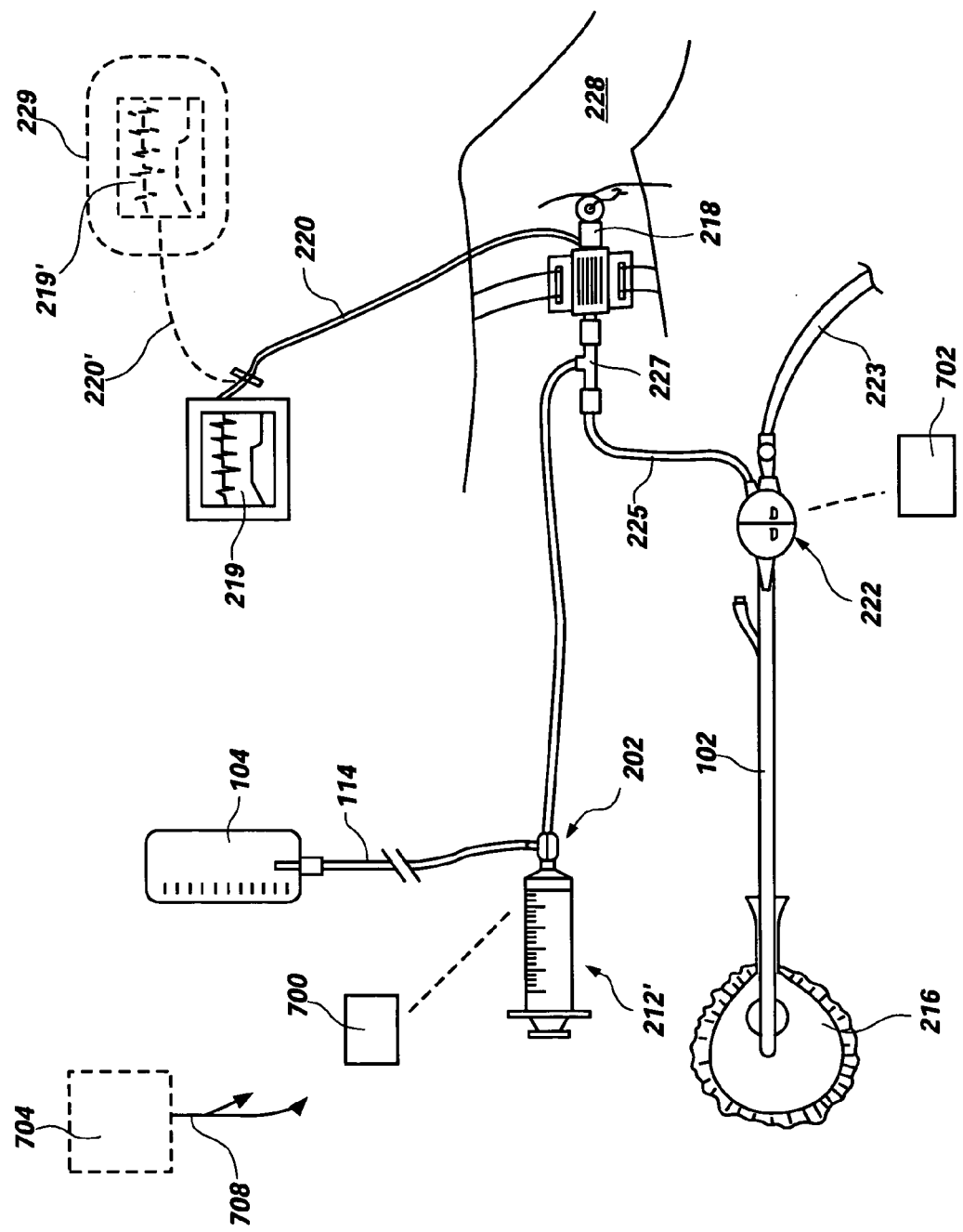
FIG. 4 illustrates a second currently preferred arrangement of equipment for measuring a patient's bladder pressure that locates a pressure transducer on the patient's leg, and is depicted in pressure measurement mode.

The arrangement to measure trends in IAP illustrated in FIG. 4 locates the pressure transducer 218 on the patient's leg 228. A finger actuated syringe, generally indicated at 212', is illustrated in combination with a flow control device 202 for use as a fluid infusion pump. The IAP valve, or urine valve 222 in FIG. 4, is illustrated as being oriented for fluid flow from fluid source 104 toward the patient's bladder 216, and for measurement of that fluid's pressure. The valve 222 may be characterized as a two-way valve, in that fluid communication may be established through valve 222 between catheter 102 and either of fluid supply conduit 225 or drain conduit 223. That is, fluid communication can be established through only two of the three potential flow paths between three port openings. Sometimes, when a urine valve, such as valve 222, is actuated from a pressure-measurement orientation to a drain orientation, a residual pressure remains in conduit 225 and undesirably is displayed on terminal 219. Therefore, sometimes a zeroing stopcock (not illustrated) is included in the pressurized fluid path, e.g. such as in a location between three-way fitting 227 and pressure transducer 218.

Illustrated valve 222 may also be characterized as providing a streamlined plumbing arrangement, in that conduits 225 and 223 are maintained in approximately parallel alignment in the vicinity of the valve 222. In contrast to an orthogonal plumbing arrangement provided by certain prior art valves, such a streamlined plumbing configuration facilitates routing of the conduits to reduce irritation to a patient. The streamlined plumbing arrangement provided by valve 222 urges conduits 225 and 223 to follow a path between the patient's legs where the conduits are most out-of-the-way, and less likely to impact negatively on patient comfort.

In the context of the instant invention, a terminal 219 encompasses any display device operable to show a representation of data for visual acquisition by a human observer. Representative terminals 219 include CRTs, LCD panels, LED arrangements, and other devices capable of producing a visible display of a representation of data, such as numbers, line plots, or bar graphs, and the like. More than one terminal 219 may be provided, with one typically being located near the patient's bed. As illustrated in FIG. 4, one or more terminals 219' may be disposed at one or more remote locations 229, such as at a central station adapted to monitor a plurality of patients, for remote monitoring of the patient by one or more health practitioners. Communication from the pressure transducer 218 to terminal 219' can be effected by wireless transmissions or through cable 220'.

Figure 5:
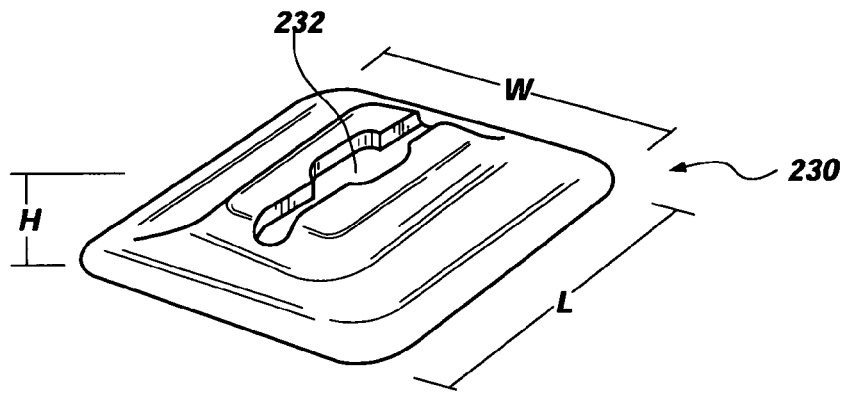
FIG. 5 is a top view in perspective of a protective housing embodied as a tray for disposition between a patient's legs.

FIG. 5 illustrates an optional housing or tray, generally indicated at 230, in which to hold portions of the assembly 200 and effective to resist patient irritation at a contact interface with the tray 230. Tray 230 effectively can shield the patient from contact with irritating portions of the assembly 200, including portions of the Foley catheter 102 and a urine discharge conduit occluding valve, if present. Tray 230 is placed in the patient's bed, typically between the patient's legs, and can shield the portion of the catheter 102 protruding from the patient.

Illustrated tray 230 can be described as having a width W, a length L, and a height H defining a volume that is somewhat pyramidal in shape. Trays 230 may be solid, or hollow. A solid embodiment within contemplation can be made from a foam material. One hollow embodiment can be formed from a plastic shell. Desirably, edges and corners of tray 230 are blunted to provide structure operable to reduce or minimize skin irritation on contact with the patient. Trays 230 may be manufactured from any material suitable for exposure to a patient's skin and operable in such a medical environment. The installed location for a tray 230 may be exposed to fecal material and other contaminants associated with a bedridden patient. Therefore, the tray 230 desirably is nonporous, or has a nonabsorbent skin, and has structure arranged to assist in cleaning. Desirably, narrow crevices are avoided to facilitate cleaning of a fouled tray 230. Certain trays 230 may be formed, at least in part, from a material that can withstand a sterilization process to permit reuse.

The volume occupied by tray 230 provides a ramp-like surround, or shield, in which is formed a receiving socket 232. Socket 232 may be structured to receive the portion of the catheter 102 protruding from the patient, and/or other structure, such as a valve 204. Tray 230 may also be adapted to orient conduits 106B and 120 for routing in substantially parallel configuration toward a patient's feet. Therefore, use of a tray 230 permits use of valves 204 having structure, such as protruding actuator levers and/or orthogonal conduit connection orientations, that would be uncomfortable to impress into a patient's skin. For example, certain trays 230 may include a socket 232 adapted to help guide fluid conduits attached to a "T" shaped two-way or three-way valve so that the conduits leave the socket 232 oriented substantially in parallel for routing those conduits in the space between a patient's legs.

Preferred trays 230 have a socket 232 adapted to hold structure associated with the catheter to aid a health practitioner during insertion of a needle into the aspiration port 125. Such a configuration for a socket 232 can be effective in reducing undesired needle sticks in both the patient and the health practitioner.

Figure 6:
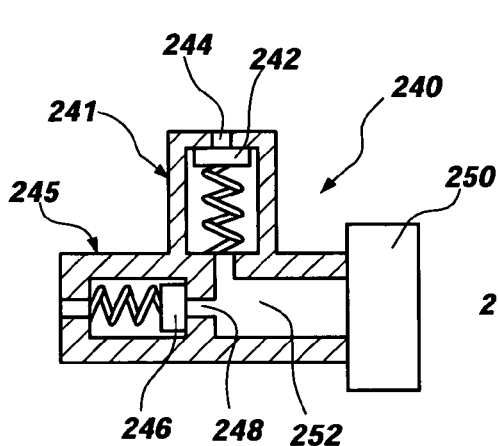
FIG. 6 is a side view, partially in section, illustrating a double check valve.
Figure 7:
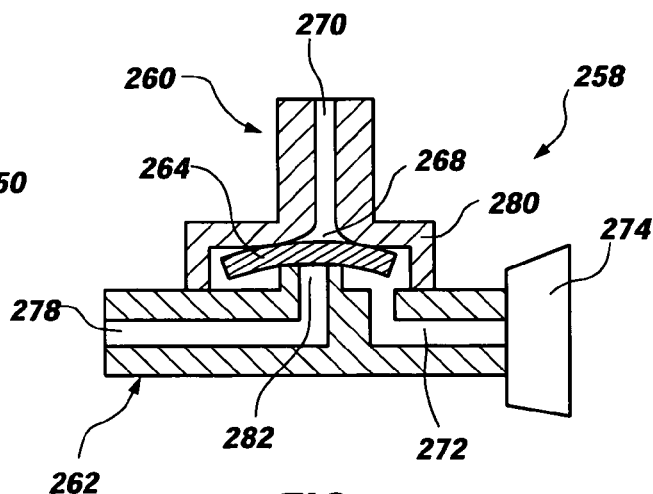
FIG. 7 is a side view, partially in section, illustrating a check-bypass valve operable as a double check valve in the invention.
Figure 8:
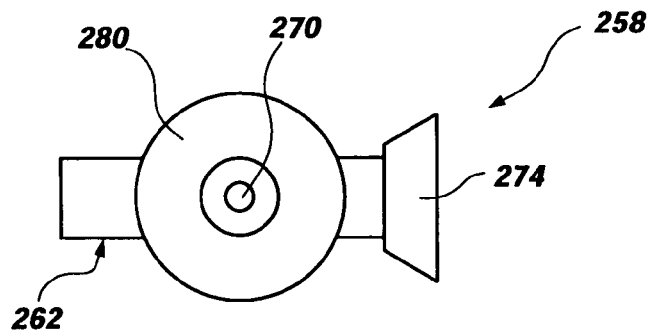
FIG. 8 is a top view of the valve of FIG. 7.
Figure 12:
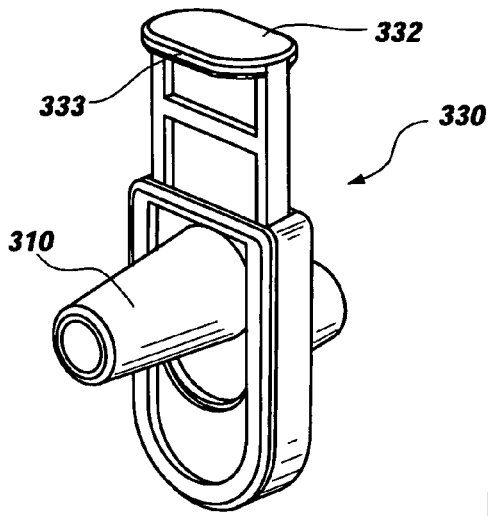
FIG. 12 is a view in perspective from a proximal end of a second urine valve.

FIGS. 6 through 8 illustrate two types of valves that are operable for use as an automatic flow-control device 202 (see FIG. 2). FIG. 6 illustrates a double check valve, generally indicated at 240. One check valve portion, generally indicated at 241, is formed by a sealing element 242 normally biased into engagement with an inlet opening or port 244. A second check valve portion, generally indicated at 245, is formed by sealing element 246 normally biased into engagement with exit port or opening 248. A pressure-cycling pump device, such as a syringe 116, may be connected in fluid communication with exit port 248 at a third port or conduit through connector 250. The syringe 116 cyclically effects the fluid pressure at a staging area 252 and thereby automatically operates the check valve portions 241 and 245 in correspondence with the high or low pressure generated by the syringe.

Of course, a fluid circuit equivalent to a fluid flow-control device, such as double check valve 240, can be formed by a pair of single check valves and a syringe 116 (or other cyclic-pressure pump) disposed between the two individual check valves. In certain embodiments, a single check valve may be included in a pressure measuring apparatus 200. In one such embodiment, the discrete check valve is located in the fluid path between a fluid source and a syringe 116 to enable multiple syringe discharges without requiring manual valve adjustments to reload the syringe with fluid.

FIGS. 7 and 8 illustrate an embodiment of a check-bypass valve, generally indicated at 258, configured for use in the instant invention. Valve 258 includes a check valve portion, generally indicated at 260, and a bypass valve portion, generally indicated at 262. Check valve portion 260 is formed by resilient member 264 biased into normally sealed engagement over orifice 268. In operation of check valve 260, fluid flows into supply port 270, and past resilient member 264, to a staging area 272. In accordance with one definition of a check valve, fluid flow in the reverse direction would cause seal member 264 to seal tighter over orifice 268, thereby further resisting the flow.

Typically, staging area 272 is in fluid communication with a syringe, such as syringe 116 illustrated in FIG. 2. A cyclic pump may alternatively be employed to vary the pressure in the staging area 272 to operate the valve 258. A syringe 116 may be attached directly to connection structure 274, or may be spaced apart from the valve 258 by use of structure such as a length of tubing.

It is currently preferred for connection structure 274 to be structured as a LUER-LOK™ type fitting, and for structure surrounding inlet port 270 and discharge port 278 to accommodate attachment of tubing by way of a press-on fit. However connection structure 274 may be structured as any other operable connecting structure, including barbs configured for press-fit reception in, or over, a conduit. Likewise, any portion of a valve 258 (or a valve 240), that is adapted for connection to a fluid conduit or other device may be structured to form a press-together fit, or to incorporate a portion of a LUER-LOK™ type joint, or a threaded connection, or as any joint providing fluid through-flow and structured to resist fluid leaks.

The illustrated bypass valve portion 262 can operate substantially as a check valve. However, under certain conditions, fluid can flow in either direction between port 278 and staging area 272. In use with the instant invention, pressurized fluid in the staging are 272 causes resilient seal member 264 to deflect into the orifice 268 of housing 280, thereby opening a flow path from staging area 272 though exit port 282 and out of discharge port 278. Contrary to a true check valve, increased fluid pressure at exit port 282 tends to open the flow path by lifting seal member 264 from engagement over exit port 282. Therefore, in certain situations, fluid could flow from discharge port 278 and into staging area 272. In that event, the fluid presumably could be refilling a syringe.

Bypass valve 262 is normally closed. Resilient member 264 is biased into sealing engagement over exit port 282 during assembly of the valve 258. Therefore, valve 262 operates as a check valve, to permit fluid flow in only one direction, until fluid pressure at exit port 282 builds to a value operable to overcome the bias in member 264. For low pressure applications, such as in measuring abdominal pressure, bypass valve portion 262 acts as a check valve.

With reference again to FIG. 2, certain preferred embodiments of a urine control valve 204 may include a valve body or housing 290 shaped to provide a comfortable interface for adjacent surfaces of a patient's skin to resist contact-induced patient discomfort. One such comfort-enhancing shape includes blunt edges and rounded corners. Valve actuation structure for a comfort-designed urine valve 204 desirably is structured to avoid protruding elements that might poke and irritate a patient.

FIGS. 9 through 11 illustrate certain details of construction of a first urine valve, generally indicated at 300, that is configured to provide a streamlined plumbing arrangement to enhance routing of conduits between a patient's legs. Valve 300 includes a valve body 302, a shuttle or valve gate 304, and a cap 306. A proximal conduit stub forming urine port 310 is placed through window 312 in cap 306 as the valve 300 is assembled. Cap 306 is typically bonded or ultrasonically welded to valve body 302, trapping gate 304 sandwiched between the cap 306 and valve body 302. Gate 304 can slide between inboard and outboard positions defined by a structural interference between urine port 310 and window 312.

Valve 300 is configured to provide two alternative, and preferably mutually exclusive, fluid flow paths through the valve. When urine port 310 is placed, as illustrated in FIGS. 9 and 10, at an inboard position in window 312, lumen 314 passing through urine port 310 is placed into alignment for fluid communication with urine discharge port 316. Grip structure 318 is provided to assist in moving gate 304 to an outboard position. At the outboard position, bore 314 is placed into alignment for fluid communication through fluid supply port 320.

FIGS. 12 through 15 illustrate a second embodiment of a valve, generally indicated at 330, that is configured to provide a streamlined plumbing arrangement to enhance routing of conduits between a patient's legs. Valves 300 and 330 are both of the type that may be characterized as transversely actuated gate valves, with a principal difference being the arrangement of gripping structure to actuate the valve gate 304. Valve 330 has gripping structure 332 arranged to provide a transversely oriented shelf 333. FIGS. 12 through 15 illustrate valve 330 oriented with gate 304 located at an outboard position to align urine port 310 for fluid communication with fluid supply port 320.

Figure 13:
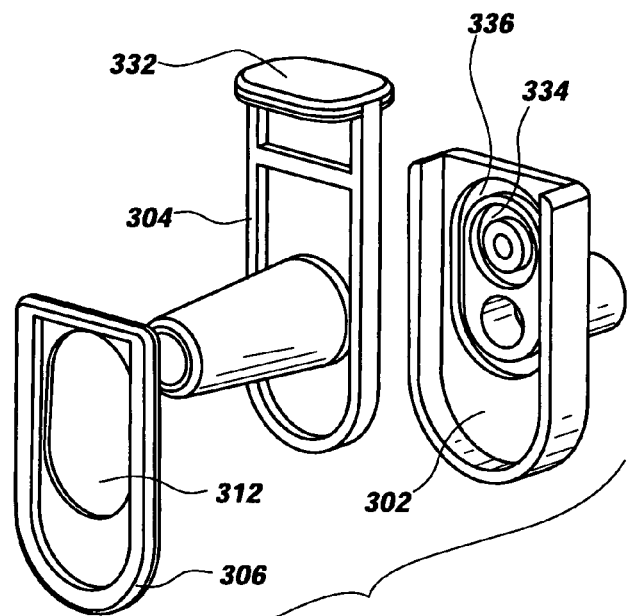
FIG. 13 is an exploded view in perspective of the urine valve illustrated in FIG. 12.
Figure 14:
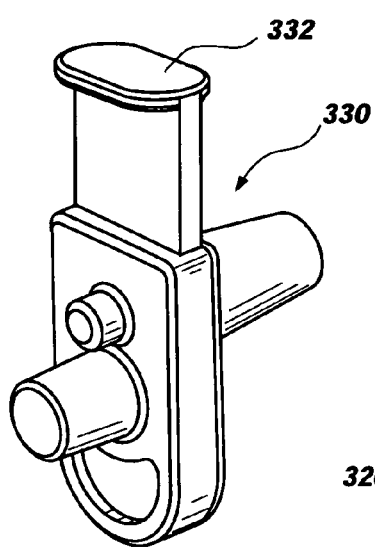
FIG. 14 is a view in perspective from a distal end of the second urine valve.
Figure 15:
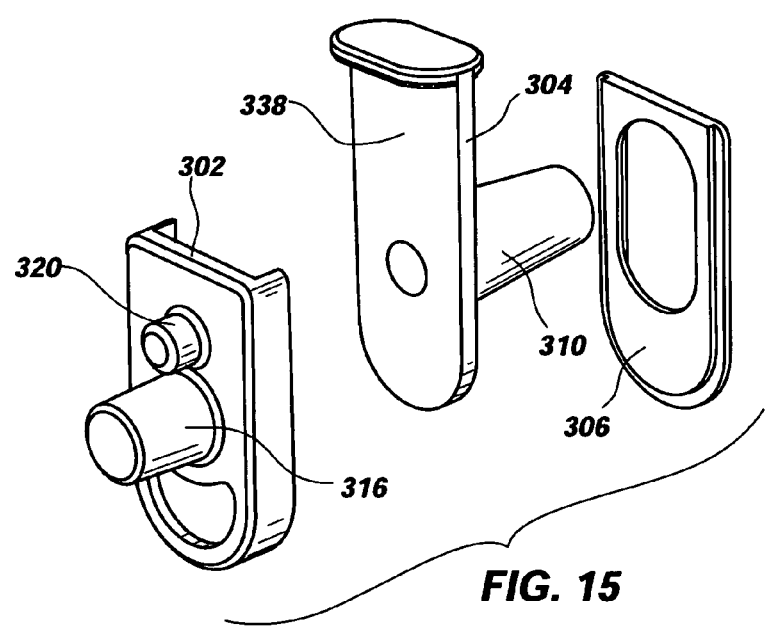
FIG. 15 is an exploded view in perspective of the urine valve illustrated in FIG. 14.

FIG. 13 illustrates one arrangement operable to resist fluid leaks from the fluid flow paths through the valve 330. Grooves 334 and 336 receive O-rings that are adapted to bear against surface 338 of gate 304 (see FIG. 15). It is alternatively within contemplation to form a raised lip about respective openings of lumens through fluid supply port 320 and urine drain 316. Such raised lips may replace the O-ring seals (not illustrated), and bear against surface 338 to form fluid-tight seal structure. In such case, and to enhance sealing, material forming gate 304 desirably would be softer than material forming a valve body 302. In any case, it is desirable to form valve seals in a single plane to minimize the amount of fluid trapped in a "dead" space between seal elements to resist chance of transfer of contamination or disease.

It is desirable to minimize back-wash of trapped fluid when pumping fluid into a patient's bladder to make an LAP measurement. Single-sided gate valves, such as valves 300 and 330, advantageously confine a minimal "dead" volume when actuated between flow path configurations. "Dead" volume is defined as the volume trapped within a valve body by seal structure, such as by an O-ring contained in groove 336 and operable as a secondary or intermediate seal. A dead volume may provide a habitat in which disease or microorganisms may grow.

For purpose of dead volume calculation, one side of a "volume" (e.g. at an end of a fluid supply conduit) may sometimes be regarded as being bounded by a plane offset from a seal surface (e.g. surface 338) and passing through an edge of a sealing O-ring. Such a volume can essentially be considered as being contained within a perimeter formed by a compressed O-ring. In one embodiment of a valve having a seal structure constructed as depicted by valves 300 and 330, the dead volume has been calculated as being about 0.0006 cubic inches (9.8 ml). In contrast, if that valve arrangement were formed to have a two-sided gate seal, the corresponding dead volume (including the passageway through the gate) would be about 0.0036 cubic inches (59 ml).

Fluid carrying conduits can be attached to urine valves, such as valves 300 and 330, when constructing a pressure measuring assembly for use on a patient, or may be affixed to one or more valve ports during a valve assembly procedure. For example, it is currently preferred to include a short length, or pigtail, of fluid supply conduit affixed to fluid supply port 320. Fluid supply conduits typically are of relatively small diameter (e.g. about 1/16 to 1/8 inches, or 1-1/2 to 3 mm, in inside diameter) to minimize priming volume. Such a conduit typically is solvent welded, or otherwise bonded to port 320. The urine drain lumen downstream of the catheter, and passing through the urine valve, desirably is of relatively larger diameter (e.g. about 3/16 to 1/2 inch, or 4.8 to 13 mm, in inside diameter) to resist occlusion during extended periods of use. A discharge end of a catheter 102, or tube section 106A (see FIG. 2), may be stretch-fit over an exterior surface of urine port 310. In some cases, an additional external clamp may further be applied over the catheter 102 or conduit 106A to augment the formed joint, and to resist decoupling the conduit from the port 310 as a bolus of fluid is injected into a patient's bladder. Similarly, a discharge conduit 106B may be attached to urine drain 316 in a plug-together fit.

FIGS. 16 through 19 illustrate a third embodiment of a valve, generally indicated at 350, that is configured to provide a streamlined plumbing arrangement to enhance routing of conduits between a patient's legs. Valve 350 is of the type that may be characterized as a rotary actuated gate valve. Valve 350 includes a valve body 352, a rotary gate 354, and a valve cover 356. Body 352 carries grooves 358 and 360 that may hold O-rings, or may provide clearance to promote sealing of lips 362 and 364 against gate surface 366.

A change in selected flow paths through the illustrated valve 350 is effected by an approximately 90 degree rotation of gate 354 relative to valve body 352. A lever 368 is trapped within arcuate slot 370 during assembly of the valve 350, and is operable to rotate gate 354 to a desired position to permit fluid communication between urine conduit 372 and either of fluid supply port 374 or urine drain 376. Assembly of valve 350 typically is accomplished by ultrasonic welding cover 356 to valve body 352. An alternative bonding process may also be used, perhaps incorporating a UV activated or other adhesive or solvent welding.

As illustrated in FIGS. 17 and 19, a fluid seal typically is formed on each of the surfaces forming opposite sides of gate 354. However, gate 354 may be made thin to minimize, or at least reduce, dead volume (trapped in a port through the gate thickness and between sealing planes) to reduce potential for culturing or transmission of disease. A redundant, or back-up, fluid seal generally is formed by an O-ring carried in groove 377. Such a seal is redundant to the fluid seals formed by O-rings carried in grooves 358 and 360, and also resists penetration of contaminants into the interior of the valve 350. Similarly, an O-ring carried in groove 378 desirably forms a seal on an opposite surface of gate 354 to resist both leaking and contamination of the interior of valve 350.

FIGS. 20 through 27 illustrate fourth and fifth valve embodiments, generally indicated at 380 and 385 respectively, that are configured to provide a streamlined plumbing arrangement to enhance routing of fluid conduits between a patient's legs. Valves 380 and 385 are also of the type that may be characterized as a rotary actuated gate valves. Valves 380 and 385 each include a valve body 388, a rotary gate 390, and a capture ring 392. Body 388 preferably carries grooves 394 and 398 in which to receive O-rings 400 and 402, respectively. Again, valve seals provided by O-rings 400 and 402 may alternatively be structured as lips or protrusions carried by body 388 and arranged to press against gate surface 404 to form a fluid resistant seal. The principal difference between valves 380 and 385 is the conformation of their distal housings, 408 and 410, respectively.

Assembly and operation of valve 380 will now be described with particular reference to FIGS. 21 and 23. O-rings 400 and 402 are placed into grooves 394 and 398 respectively. Then a rotary gate 390 is placed onto the exposed portions of the O-rings. Gate 390 is oriented to locate detente 414 in the space provided by arcuate slot 416. Gate 390 can therefore rotate between limits formed by a structural interference formed between detente 414 and opposite ends of arcuate slot 416. Valve body 388 is then joined to retainer ring 392 to capture, and permit rotation of, the gate 390. Distal ring 417 rides on circumferential bearing surface 418 to hold gate 390 in sealing axial engagement with O-rings 400 and 402. A notch in capture ring 392, generally indicated at 419, provides clearance for detent 414. It is also within contemplation to form a detente 41 with a step shape to accommodate a ring 417 that has an uninterrupted circumference.

Infiltration of external contamination to the inside of a valve 380 is resisted by O-ring 420. O-ring 420 is received on shoulder 422 carried on a proximal end of capture ring 392. A distal end 426 of proximal housing 428 is adapted to ride on O-ring 420, and to compress the O-ring 420 against shoulder structure 422 to seal the valve 380. It is currently preferred to form a valve, such as valve 380, to facilitate cleaning the exterior surface of the valve 380. Therefore, it is desirable to avoid crevices where contaminants may remain subsequent to wiping the exterior surface of the valve 380. The seal formed by O-ring 420 is adapted to facilitate cleaning of a patient's bodily excretions from an exterior of the valve 380.

In general, proximal housing 428 can be held in an assembled axial position in a valve 380 by forming a joint between structure carried by the housing 428 and structure carried by the gate 390. As illustrated, distal conduit extension 430 (FIG. 23) from urine port 432 is affixed to socket 434 (FIG. 21) carried on gate 390. Similarly, a distal end of post 440 is attached to socket 442. Gate 390 is held by post 440 and conduit 430, and rotates with housing 428.

With reference to FIG. 23, a flow path through the urine valve 380 includes lumen 444 extending through urine port 432 and extension conduit 430. Lumen 444 is fixed in fluid communication with aperture 446 passing through gate 390 during assembly of valve 380. The remainder of a flow path through valve 380 is dependent upon the rotation orientation of gate 390. At one gate orientation, aperture 446 is placed into fluid communication with lumen 448 extending through urine discharge port 450. Such an orientation for valve gate 390 is the typical valve configuration, and permits continual draining of urine from an installed urinary catheter. At another gate orientation, aperture 446 is placed into fluid communication with lumen 452 extending through fluid supply port 454. Therefore, fluid communication through two-way urine valve 380 can be provided either through lumen 448 or lumen 452. The latter gate orientation permits a fluid bolus to be injected into the patient's bladder for LAP measurement.

Proximal housing 428 and distal housing 408 provide somewhat of a torpedo-shape to the urine valve 308. A torpedo-shape enhances patient comfort by reducing or minimizing protruding portions from a valve that might irritate the patient's skin when contacted. Preferred torpedo-shapes generally are defined by valve structure that is somewhat elongate and cylindrical. Advantageously, such valve structure may also taper to a reduced size at proximal and distal ends. A torpedo-shaped valve can also operate to streamline fluid conduit plumbing in the vicinity of the valve. Such structure can be contrasted to commercially available two-way valves that generally orient one conduit connection at a right angle to a pair of typically in-line conduit connections, forming a "T" shape.

It is currently preferred to include sections of tubing, such as tubing 223 and 225 in FIG. 3, affixed to a valve such as valve 380. When present, a conduit 225 can be solvent welded inside lumen 452. A conduit section corresponding to at least a portion of urine drain 223 illustrated in FIG. 3, can be similarly installed inside lumen 448, or may be stretched in a plug fit over port 450. Of course, such portions of fluid conduits would first be threaded through apertures 456 and 458 (see FIG. 20) in distal housing 408. Subsequent to affixing such conduit portions in place on valve body 388, distal housing 408 can be attached to valve body 388.

Desirably, apertures 456 and 458 are sized in close conformance to a diameter of conduit sections passing therethrough. Close agreement in size between the aperture and the conduit it surrounds facilitates maintaining the valve 308 in a clean state. It is within contemplation also to provide a plug or stopper to occlude any open portions of an aperture between a conduit and an aperture wall. Valve 385, illustrated in FIGS. 24 through 27, has a distal housing specifically shaped to form apertures 460 and 462 that are in such close agreement with a respective fluid supply conduit and a urine drain conduit.

Certain valves, such as torpedo valves 380 and 385, benefit from the presence of indicia to show the current flow path through the valve. In valve 380 (see FIG. 21) an indicator flap 466 is placed into axial agreement with either alignment indicator 468 or 470 to place valve 380 into drain mode or LAP mode, respectively. Indicators 466, 468, and 470 are illustrated as protruding slightly from a surface of housings 428 and 408 to provide tactile and visual feedback to a valve operator. Alignment flaps 472 and 474 carried on proximal and distal housings of valve 385 are placed into axial agreement to place valve 385 into a urine drain configuration. Such indicators 472 and 474 provide visual feedback to remind a health practitioner to return a valve 385 to a urine drain mode.

It currently is currently preferred for a urine valve to maintain a "smooth" or "blunt" contact area, at a potential patient interface, when rotated to either pressure measurement or urine draining positions. Also, the indicator structures 466-474 desirably have a relatively low profile to avoid inflicting patient discomfort if brought into contact with the patient's leg. It is also within contemplation to apply areas of different color to portions of the respective housings to alternatively, or additionally, indicate a valve flow path setting. It is further within contemplation to provide written indicia to spell out a flow path corresponding to a particular valve orientation.

It is currently preferred to injection mold valve components in straight-pull, simple molds to reduce mold-making and attendant manufacturing costs. Valves may be formed from a variety of medical grade plastics, including polycarbonate, ABS, acrylic, and polyethylene. O-ring seals may be formed from suitable rubber-like materials, with silicone currently being preferred. A variety of bonding procedures are operable to join valve components to form a valve assembly, including plastic welding techniques such as solvent, ultrasonic, friction, shear, and heat welding, as well as adhesive bonding techniques.

With reference again to FIGS. 20 and 21, sometime a hose barb, generally indicated at 478, desirably is included on a urine port 432 to resist decoupling of a urinary catheter 102 connected to the port 432. One way to include such barb structure 478 in a straight-pull molded part is as the illustrated add-on ring 480. Ring 480 typically is affixed to port 432 with an adhesive procedure, although welding or other attachment constructions are also effective. Of course, an alternative urine port 432, having an integral barb and manufactured as a separate component, could be affixed to a housing 428.

As an additional safeguard to resist decoupling of a urinary catheter 102, a clamp 484 may additionally be provided for installation on top of catheter 102 once the catheter 102 is installed in a press-fit over the barb structure 478. A clamp 484 desirably is both self-biased and structured to avoid protrusions that might injure or bother a patient on contact. An alternative clamp 484 can be made from a piece of tape that is snugly wound around an installed conduit, such as the discharge end of catheter 102.

Figure 30:
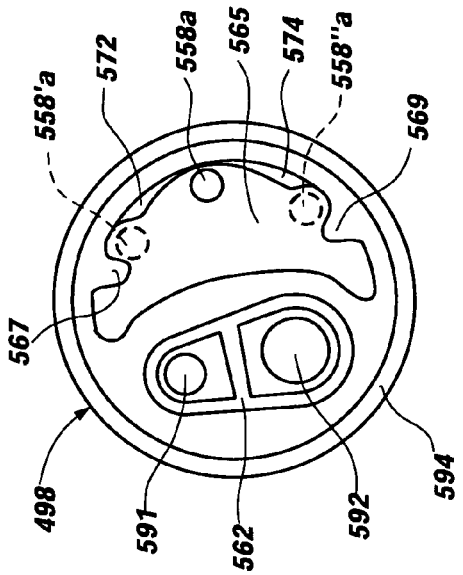
FIG. 30 is a plan view taken through the section line 30-30 in FIG. 29 and looking in the direction of the arrows.
Figure 28:
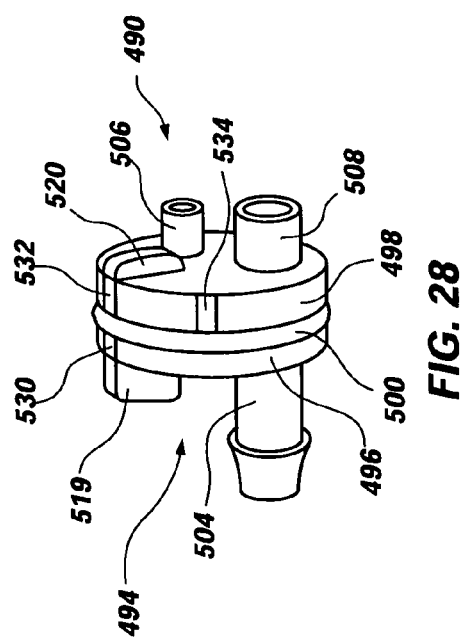
FIG. 28 is a view in perspective from the drain end of a sixth preferred urine valve that is placed in a urine draining configuration.

Structural arrangements forming currently preferred 6th and 7th urine valves will now be discussed with reference to FIGS. 28-30. The 6th illustrated valve, generally indicated at 490, has a compact and blunt valve body, generally indicated at 494, to facilitate placement of the valve between a patient's legs, and to resist imparting contact-induced injury to the patient. A valve 490 desirably has a maximum body diameter size that is on the order of about 1 inch (25.4 mm), or even less. Desirably, urine valves for use in IAP measurement installations, such as illustrated valve 490, are structured to facilitate routing associated fluid conduits in a substantially parallel configuration for their tidy disposition near a patient's groin area.

Valve body 494 includes proximal housing portion 496 and distal housing portion 498. A body seal, such as O-ring 500, desirably is provided to resist infiltration of contaminant materials into an interior of valve 490, and can operate as a redundant seal to avoid fluid leaks from the valve. The proximal and distal housing portions are adapted to rotate with respect to one another operably to align a flow path through urine entrance port 504 selectively for fluid communication with either of pressure measurement port 506, or drain port 508.

Figure 29:
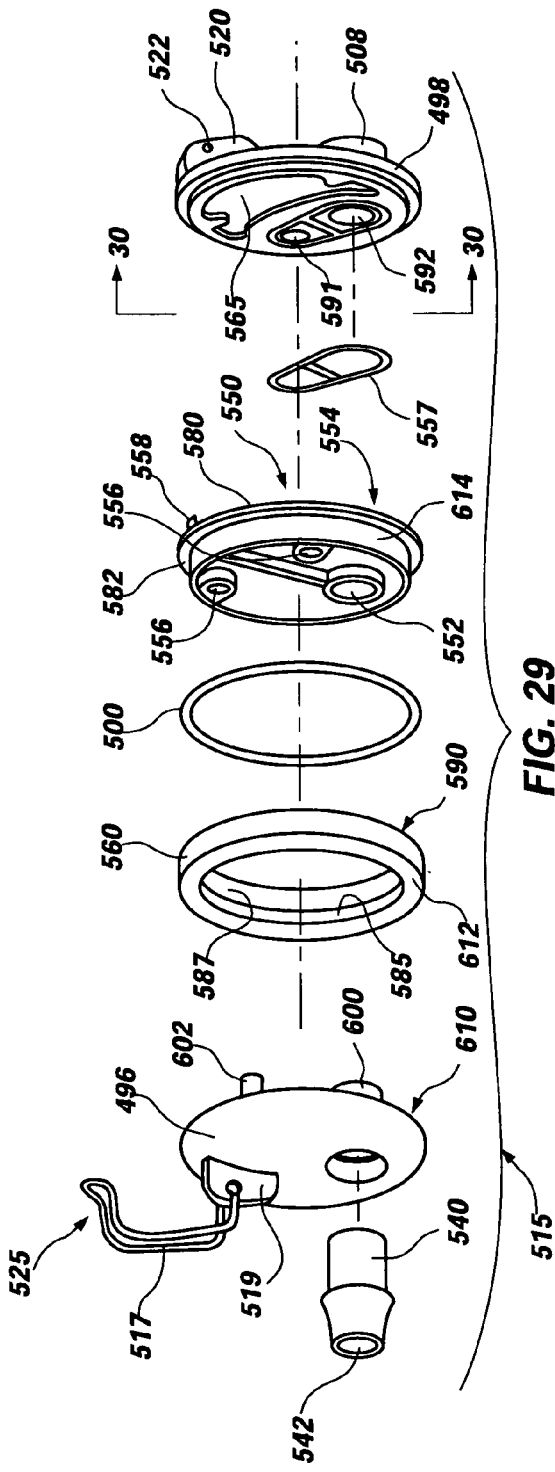
FIG. 29 is an exploded assembly view in perspective from the proximal end of a seventh urine valve that is similar to the valve illustrated in FIG. 28.

FIG. 29 illustrates an exploded assembly view of an alternate valve, generally indicated at 515. Valve 515 is similar to valve 490, but also includes a mechanical lockout structure 517. Lockout structure 517 includes a wire framework rotatably anchored to the proximal alignment wing 519. Wire 517 can index in captured relation with distal alignment wing 520 only when the valve 515 is oriented in a urine drain configuration. A detent 522 may be provided to interface with a capture area generally indicated at 525 to help define a captured engagement. The addition of lockout structure adds an additional step to help a health practitioner remember to return a urine valve to a drain position subsequent to performing a manual IAP measurement. Of course, it is recognized that a wide variety of structure, other than the single illustrated embodiment 517, can be arranged to perform an equivalent lockout function.

With reference again to FIG. 28, it is sometimes desirable to provide redundant alignment indicating structure for visual verification of an orientation of a urine drain valve. It is currently preferred to provide a marker band 530 having a first color and disposed on the proximal housing 496. A signal band 532 is disposed on the distal housing portion 498 for alignment with the marker band 530 when the valve 490 is oriented to a drain configuration. Signal band 532 desirably has the same first color as the marker band 530 to further convey alignment information to a health practitioner. Marker and signal bands, such as 530 and 532 respectively, can extend along a portion of their housings, and along alignment structure, such as alignment wings 519 and 520 respectively, to provide a larger visible feedback. A second signal band 534 is disposed on the distal housing 498 for alignment with marker band 530 only when valve 490 is oriented to a pressure measurement configuration. Desirably signal band 534 has a second color that is distinct from the first color. It is currently preferred for the first color to be green, and the second color to be red. Colored bands can be applied to a urine drain valve using known operable procedures.

Manufacture of a valve 515 can be explained in detail with reference to FIGS. 29 and 30. A variety of known fastening techniques may be employed to connect individual elements, including solvent welding, and ultrasonic welding. Valve 515 includes an inlet port 540 that is adapted for connection to tubing, such as a urinary catheter 102. Opening 542 desirably is sized in harmony with a diameter of the catheter to avoid creating flow restriction and to resist collection of debris or coagulation passed by a patient in which such a catheter may be installed. Desirably, a conduit, having a substantially uniform diameter in harmony with a diameter of opening 542, is provided as a drain path through the valve 515. A preferred such diameter is about 3/16 inches (4.8 mm), or larger. A distal portion of a stem of the inlet port 540 is permanently affixed in fluid-tight engagement inside receiving socket 545 to proximal body portion 496.

A proximal face of valve gate 550 carries an assembly socket 552 in fluid communication with an aperture 554 that is disposed on a gate distal face. The proximal face of gate 550 also carries one or more assembly sockets 556. The illustrated assembly sockets 552 and 556 are disposed to form a roughly equilateral triangle. A portion of the distal face of gate 550 typically is substantially flat to provide a radially disposed sealing plane surface structured to cooperate with one or more sealing elements, such as B-ring 557. B-ring 557 typically is injection molded from a medical grade elastomeric substance, and operates to seal a plurality of orifices and reduces part count in a valve 515. Desirably, some sort of structure is included to provide valve orientation feedback, such as distally protruding orientation post 558.

A proximal side of distal body portion 498 carries structure adapted to cooperate with structure of the gate 550, B-ring 557, and capture ring 560. A socket or channel 562 is provided to receive the sealing member 557. Cooperating position indication structure, such as socket 565 is provided to interface with orientation post 558. Socket 565 is configured to provide valve rotation stop structure, including drain position stop 567 and measurement position stop 569.

Certain embodiments of urine valves carry optional structure operable to provide a tactile feedback to a valve operator to indicate complete rotation of a valve to a desired position. One such arrangement is illustrated in FIG. 30, and includes one or more ramp structures 572 and/or 574. Ramps 572 and 574 are arranged to cause a small structural interference with post 558*a*. Such an interference can be formed in a radial direction, as illustrated, or in an axial direction, e.g. to interfere with a distal end of post 558. As illustrated, when valve 515 is rotated to move post 558*a* to a drain position at 558*a*', post 558*a* engages and scrapes past ramp 572 gradually increasing an interference, until post 558*a* is disposed substantially in the drain position. When near the drain position, the ramp drops off in a radial direction and quickly reduces the formed structural interference, producing tactile feedback in the form of a sensation that is perceptible to a valve operator, and which may include an audible "click." A similar interference is generated when moving post 558*a* past ramp 574 to the pressure measurement position 558*a*". At the illustrated position 558*a*, a "sweet spot," offering reduced resistance to valve rotation, may be provided to facilitate assembly of the valve, and to produce additional tactile feedback relating to valve orientation.

With reference again to FIG. 29, gate 550 is maintained in a substantially fixed axial relation to distal body portion 498 by way of capture ring 560. Gate 550 carries a lip 580 disposed about its perimeter which forms a shoulder area 582. The lip 585 of ring 560 forms a cooperating shoulder area 587 that engages shoulder area 582 and captures lip 580 of gate 550 in an axial direction, but permits rotation of gate 550. A distal surface 590 of ring 560 is permanently affixed to distal body portion 498 on assembly of the valve 515. Ring 560 is configured so that upon assembly to body 498, the seal member 557 is slightly compressed to form an operable fluid seal for aperture 591 and aperture 592. In the illustrated embodiment, surface 590 preferably is ultrasonically welded at receiving shoulder area 594 of distal body 498. Receiving shoulder area 594 provides a centering function to facilitate placement of ring 560 in relation to body 498 during manufacturing. However, it is recognized that shoulder 594 could be eliminated and a centering jig used instead.

Proximal body portion 496 is permanently affixed to gate 550 by way of assembly conduit 600, and one or more assembly posts 602 (only one of which is visible in FIG. 29). It is currently preferred to provide a pair of posts 602 to form a solid connection between a body 496 and gate 550, and to resist deflection of body 496 in an axial direction when actuating a valve 515. The three points of support disposed in a triangular arrangement and provided by posts 602 and conduit 600 help to resist deflection of body portion 496. Conduit 600 is received in socket 552, and posts 602 are received in sockets 556 and 558. Receipt of assembly structure in socket structure aides in maintaining an alignment of valve components during valve assembly. It currently is preferred ultrasonically to weld the gate 550 to body 496.

During assembly of the gate 550 to the body 496, an optional O-ring 500 is trapped to create a seal between distal surface 610 of body 496 and proximal surface 612 of ring 560. An inside diameter of O-ring 500 typically engages surface 614 of gate 550. An O-ring 500 can provide a smooth actuation "feel" to a user as body 496 is rotated with respect to body 498 to actuate valve 515 between desired operation positions.

With reference to arrangements to measure IAP such as illustrated in FIGS. 2-4, it has been found that, sometimes, a residual pressure remains in conduit 120 or 205 subsequent to placing the urine valve into urine draining mode. The residual pressure is undesirable, as such pressure is not a true reflection of the patient's bladder pressure. Several arrangements are operable to avoid such undesired residual pressure. First, a zeroing stopcock can be disposed in the pressurized fluid path, as previously described. Second, a two-way urine valve may be configured, at a sweet spot between open and closed positions, to permit the pressurized saline to drain from a pressurized aperture into a drain aperture as a fluid flow path within a valve body. Third, a channel can be provided to provide fluid communication from the pressurized fluid aperture, such as aperture 591 in FIG. 29, to a drain aperture, such as aperture 592, when the valve is rotated to a urine drain orientation. Fourth, a pressure port can be provided in fluid communication with a urine drain conduit upstream from a fluid occluding device. In the latter configuration, the occluding device is actuated to occlude the urine drain conduit only during pressure measurements. When the drain conduit is reopened, the pressurized saline drains along with any fluid in the patient's bladder. Any pressure showing on a display terminal 219 desirably would then reflect actual bladder pressure of the patient.

Figure 31:
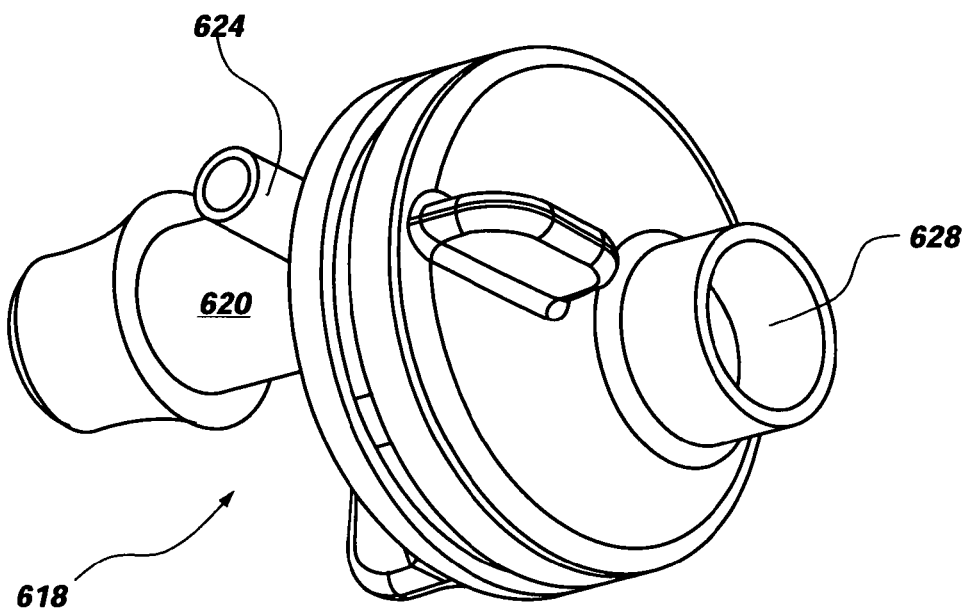
FIG. 31 is a view in perspective from the distal end of an alternative eighth urine valve having an upstream pressure port and with the valve being actuated to permit making a IAP measurement.
Figure 32:
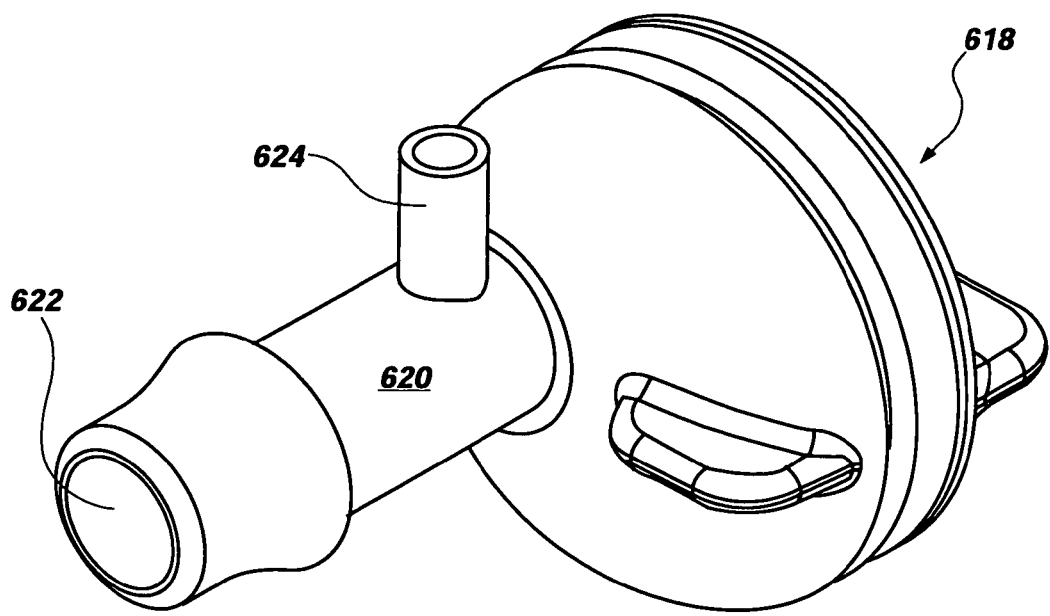
FIG. 32 is a view in perspective of the valve illustrated in FIG. 31, looking from the proximal end, and with the valve in an open drain configuration.

FIGS. 31 and 32 illustrate one valve arrangement, generally indicated at 618, that provides the desired pressure transducer performance. A male fitting 620 is adapted for connection to a discharge end of a urinary catheter, and provides a drain conduit 622 for bladder output. A saline port 624 provides fluid communication between drain conduit 622 and a pressurized saline source having an associated pressure transducer positioned to measure the pressure of the saline. Valve 618 is a simple on/off valve, and combines a "T" fitting into its intake port 620 to facilitate assembly of an IAP apparatus. When an IAP measurement is made, the valve 618 is oriented as illustrated in FIG. 31 to occlude the urine drain path through conduit 628. When the measurement is accomplished, the valve 618 is rotated to the orientation illustrated in FIG. 32 to open a drain path through conduit 628. Any excess pressure in conduit 624 is released by draining into conduit 628. As a result, a pressure transducer in fluid communication with conduit 624 will indicate an actual bladder pressure for the patient.

Figure 33:
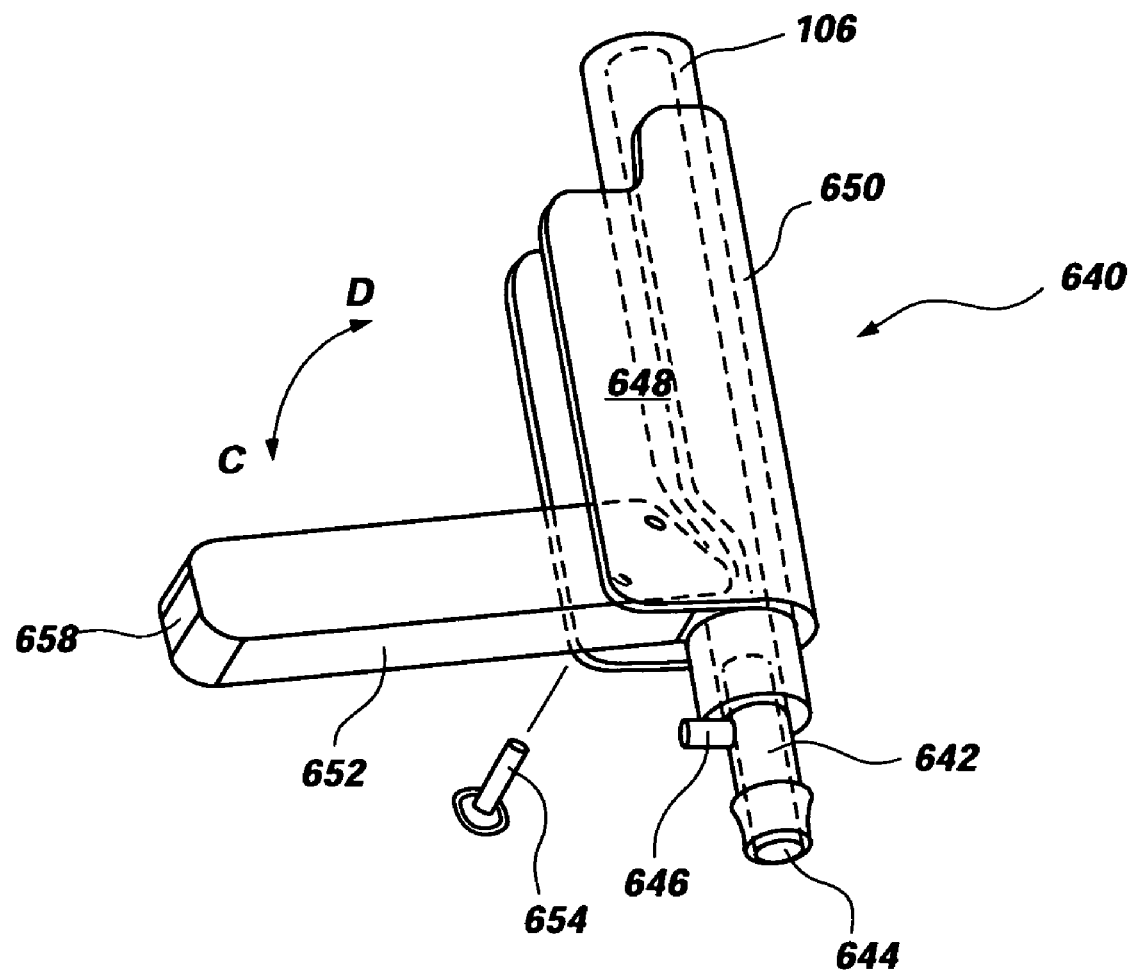
FIG. 33 is a view in perspective of another alternative urine valve arrangement.

An alternate valve arrangement, similar to the arrangement in FIGS. 31-32, is shown in FIG. 33. The alternative valve arrangement, generally indicated at 640 includes a combination of a male fitting 642 adapted for connection to a discharge end of a urinary catheter, and provides a drain conduit 644 for bladder output. A saline port 646 provides fluid communication between drain conduit 644 and a pressurized saline source having an associated pressure transducer positioned to measure the pressure of the saline. Clamp valve portion 648 includes a generally "U"-shaped frame 650, and a toggling lever 652. Lever 652 is arranged to pivot about an axle, such as removable pin 654. Removable pin 654 permits the valve 648 to be installed transversely onto a conduit. It is within contemplation alternatively to provide a permanent axle, and to feed a conduit axially through frame 650.

Clamp valve 648 is illustrated in a closed position to occlude urine drain conduit 106. Free end 658 of lever 652 has been rotated, in the direction indicated by arrow head C, to the fully closed position for an LAP measurement. Clamp valve 648 is opened to permit draining of the fluid bolus and urine output by rotating free end 658, in the direction indicated by arrowhead O, until lever 652 is disposed parallel to conduit 106 to reduce space occupied by valve 648 and reduce patient discomfort.

Lever 652 and body 650 cooperate to indicate a valve condition—open or closed. In addition to the feedback notice provided by misalignment of lever 652 and an axis of conduit 106, a color warning may additionally be provided. Those portions of lever 652 that are visible when valve 648 is not in a fully open configuration can carry a warning color. Such warning color would be obscured by sides of the "U"-shaped body 650 when lever 652 is disposed in the fully-open drain configuration.

It is an important safety event for a urine valve to be returned to an open or urine-draining configuration subsequent to performing an IAP measurement. It is within contemplation for a urine valve to be provided with structure arranged automatically to accomplish such return. One structural arrangement to effect an automatic return to an open-valve configuration stores energy imparted to open the valve for a period of time, and then uses the stored energy to close the valve. Electromechanical actuators, such as solenoid driven mechanisms, may be harnessed to effect automatic valve actuation under machine or automated control.

In general, urine valves operable in the present invention may be actuated by human action, hydraulically, or electro-mechanically. Infusion pumps may similarly be actuated. The entire IAP procedure lends itself to automation to remove a tedious, error prone, burden from health practitioners. With reference to FIG. 4, the pumping system including syringe 212' can be replaced by an automated infusion pump 700. Similarly, the urine valve 222 can be replaced by an automated urine valve 702. The infusion pump 700 and urine valve 702 can be placed under the control of a control device 704, which can be programmable. Control device 704 can be arranged to communicate with pump 700 and valve 702 using wireless transmissions or wires 708. The collected LAP data is then displayed at convenient locations, such as one or more of terminals 219 and 219'.

While the invention has been described in particular with reference to certain illustrated embodiments, such is not intended to limit the scope of the invention. The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An apparatus for measuring hydraulic pressure in the bladder of a medical patient comprising:
   a catheter adapted for draining urine from said patient into a drain conduit;
   a container of fluid;
   a first fluid path between said container of fluid and a discharge end of said catheter;
   a pump disposed to effect a pressure on fluid in said first fluid path;
   a pressure transducer arranged to measure a pressure of said fluid in said first fluid path at a location downstream of said pump; and
   a drain valve defining, at most, two fluid flow paths therethrough, each such flow path extending from a valve housing entrance to a valve housing exit and being configurable to permit uninterrupted flow of fluid the entire length there-between, the drain valve being operable to occlude said drain conduit while permitting fluid flow through said first fluid path, said valve being configured to remain in association with said drain conduit when said valve is in a configuration to permit fluid flow through said drain conduit, the valve comprising structure configured to cause routing of a length of the first path, on the container-side of the valve and in the vicinity of the valve, to be disposed substantially in parallel with both of:
      a first length of the drain conduit at a valve entrance, and;
      a second length of the drain conduit at a valve exit.

2. The apparatus of claim 1, said valve comprising:
   a multi-way valve comprising:
      a first flow portion disposed in said first fluid path and arranged to receive fluid from said container;
      a second flow portion disposed in a second fluid path configured as a drain for said catheter; and
      a third flow portion disposed in said first fluid path for fluid communication with a urine discharge end of said catheter;
   wherein:
      said multi-way valve is operable selectively to resist fluid flow between said third flow portion and said second flow portion; and
      said multi-way valve is configured to resist access of ambient air into the second flow portion during conventional operation of the valve.

3. The apparatus of claim 2, wherein:
   a urine draining lumen forming a flow path through said valve has a substantially uniform diameter in excess of about 3/16 inches (4.8 mm), and;
   a sealing element of said multi-way valve is structured to contain a dead volume of less than about 0.0006 cubic inches (0.01 ml).

4. The apparatus of claim 1, said drain valve further comprising:
   a proximal body portion comprising a single valve entrance port through which fluid may communicate on a path extending through said valve, a first alignment structure, and an axial connection structure;
   a distal body portion structured in harmony with said proximal body portion to permit relative motion there-between subsequent to assembly of said valve, said distal body portion comprising:
      a second alignment structure disposed for cooperation with said first alignment structure to indicate a valve fluid-flow configuration;
      a first aperture in fluid communication with a first distal fluid port through which fluid may communicate on a path extending through said valve; and
      a second aperture in fluid communication with a second distal fluid port through which fluid may communicate on a path extending through said valve;
   a rotatable valve gate comprising a conduit having a third aperture disposed on a distal gate surface and in fluid communication with said valve entrance port and selectively positionable for fluid communication with either of said first and second apertures, a perimeter of said gate being trapped by structure permanently affixed to said distal body portion effective to maintain said gate in a substantially fixed axial relation to said distal body portion, with structure associated with said gate being permanently affixed to said axial connection structure carried by said proximal body portion; and
   valve seal structure disposed selectively to form a leak resistant seal for fluid communicating between said first aperture and said third aperture, and between said second aperture and said third aperture.

5. The apparatus of claim 4, further comprising:
   a valve body seal disposed between said proximal body portion and said distal body portion to resist contaminant infiltration into an interior of said valve.

6. The apparatus of claim 4, further comprising:
   positive stop structure disposed to resist displacement of said gate beyond a fully actuated position.

7. The apparatus of claim 6, wherein:
   said positive stop structure comprises a distally protruding orientation post carried by said gate and cooperating structure associated with said distal body portion.

8. The apparatus of claim 4, further comprising:
   fluid-flow position indicating structure comprising:
      a first area disposed on said proximal body portion and having a first color;
      a second area disposed on said distal body portion and having said first color; and
      a third area disposed on said distal body portion and having a second color;

wherein:
alignment of said first and second areas corresponds to said valve being at a preferred fluid-flow orientation, and alignment of said first area and said third area corresponds to said valve being at a second fluid-flow configuration.

9. The apparatus of claim 4, further comprising:
vibration inducing structure disposed to provide tactile feedback to a user operable to indicate complete actuation of said valve to a fluid-flow configuration.

10. The apparatus of claim 9, wherein:
said vibration inducing structure comprises structure associated with a positive stop structure disposed to resist displacement of said gate beyond a fully actuated position.

11. The apparatus of claim 9, wherein:
said vibration inducing structure is arranged to form a structural interference between an element associated with said distal housing and an element associated with said gate.

12. The apparatus of claim 9, wherein:
said vibration inducing structure comprises ramp structure associated with said distal housing and arranged to form a structural interference with an orientation post carried by said gate.

13. The apparatus of claim 4, further comprising:
lockout structure arranged for actuation only when said, valve is in a particular fluid-flow configuration.

14. The apparatus of claim 4, further comprising:
a return mechanism structured and arranged automatically to return said gate to a urine-draining configuration subsequent to lapse of a defined period of time from actuation of said valve to a drain occluding position.

15. A preassembled apparatus adapted to assist in measuring the pressure in a bladder of a patient to infer the intra-abdominal pressure of that patient through a urinary catheter installed in the patient, comprising:
a bag connector operable to couple to a saline bag effective to drain saline solution from said bag;
a first conduit in fluid communication with said bag connector and operable to transport said saline solution to an infusion pump;
said infusion pump being configured and arranged to urge said saline solution in a pressurized fluid path toward a urine valve;
a second conduit having a first end coupled to said infusion pump and a second end mechanically associated with said urine valve;
a transducer connector coupled to said second conduit, configured and arranged to couple with a pressure transducer to permit placing said pressure transducer into fluid communication with said saline solution in said second conduit; and
said urine valve being configured at a valve entrance end to removably couple for fluid communication with said catheter, said urine valve defining, at most, two fluid flow paths there-through, each such flow path extending from a valve housing entrance to a valve housing exit and being configurable to permit uninterrupted flow of fluid the entire length there-between, said valve being coupled to a urine drain conduit and operable to occlude a drain path for urine from said catheter, the urine valve comprising structure configured to cause routing of a length of the pressurized fluid path, on the fluid source-side of the urine valve and in the vicinity of the urine valve, to be disposed substantially in parallel with both of a first length of the drain conduit at a valve entrance, and a second length of the drain conduit at a valve exit.

16. The apparatus of claim 15, further comprising a package of material arranged to hold said assembly and operable to maintain sterility of said assembly during storage and transport of said assembly inside said package.

17. The apparatus of claim 15, said urine valve comprising:
a proximal body portion comprising a single valve entrance port, a first alignment structure, and axial connection structure;
a distal body portion structured in harmony with the proximal body portion to permit relative motion therebetween subsequent to assembly of the valve, the distal body portion comprising:
a second alignment structure disposed for cooperation with said first alignment structure to indicate a valve fluid-flow configuration;
a first aperture in fluid communication with a first valve discharge port; and
a second aperture in fluid communication with a second valve discharge port;
a rotatable valve gate comprising a conduit having a third aperture disposed on a distal gate surface and in fluid communication with said valve entrance port and selectively positionable for fluid communication with either of said first and second apertures, a perimeter of said gate being trapped, to permit rotation of the gate about an axis passing in an axial direction through both of the proximal body portion and the distal body portion, by structure permanently affixed to said distal body portion effective to maintain said gate in a substantially fixed axial relation to said distal body portion, with structure associated with said gate being permanently affixed to said axial connection structure of said proximal body portion; and
valve seal structure disposed selectively to form a leak resistant seal for fluid communicating between said first aperture and said third aperture, and between said second aperture and said third aperture.

18. The apparatus according to claim 1, further comprising:
a second fluid path defined by structure configured to permit fluid communication between said drain portion of said catheter and a fluid receiver; wherein:
first and second apertures, opening to portions of respective first and second flow paths through said drain valve, are disposed on a first surface; and
a valve core element comprises a second surface structured in cooperation with said first surface such that a third aperture disposed on said second surface can be aligned to form a leak resistant seal for fluid communication through either of said first aperture and said second aperture, said third aperture opening to a portion of a flow path extension for either of said first flow path and said second flow path; and
said leak resistant seal comprises:
a first O-ring disposed to encompass said first aperture; and
a second O-ring disposed to encompass said first aperture and said second aperture.

19. An apparatus for measuring hydraulic pressure inside the urinary bladder of a medical patient, the apparatus comprising:
a first fluid pathway in fluid communication with a source of fluid on a first end thereof and a catheter on a second end thereof, said catheter being structured for draining urine from a medical patient's urinary bladder into a drain conduit;

a pump intercooperated with first fluid pathway disposed to urge flow of fluid through said first fluid pathway;

a pressure transducer in fluid communication with said first fluid pathway for measuring fluid pressure of fluid within said first fluid pathway at a location disposed downstream of said pump; and a drain valve, coupled to said first fluid pathway, operable to resist fluid flow through said drain conduit, the drain valve defining, at most, two fluid flow paths therethrough, each such flow path extending from a valve housing entrance to a valve housing exit and being configurable to permit uninterrupted flow of fluid the entire length there-between, the valve comprising structure configured to cause routing of a length of the first fluid pathway, on the fluid source-side of the valve and in the vicinity of the valve, to be disposed substantially in parallel with both of a first length of the drain conduit at a valve entrance, and;

a second length of the drain conduit at a valve exit.

20. The apparatus according to 19, wherein:

a first portion of said first fluid pathway comprises a first length of lumen disposed adjacent a control location at which said drain valve may act to resist fluid flow through said drain conduit;

said drain conduit comprises a second length of lumen structured to permit at least intermittent communication of fluid through said control location, wherein:

downstream fluid flow through said first length of lumen and extending through said second length of lumen causes fluid flow through said first length of lumen that is, from the point of view of an external observer, substantially parallel to, and in the opposite direction from, fluid flow through said second length of lumen.

21. The apparatus according to 20, further comprising:

structure configured and arranged effective to hold said first length of lumen in a substantially fixed relationship in space with respect to said second length of lumen.

22. The apparatus according to 19, wherein:

the valve housing entrance is carried on a distal valve body portion of a valve housing;

a valve housing exit is carried on a proximal valve body portion of the valve housing; and the distal valve body portion is structured in harmony with the proximal valve body portion to permit relative motion there-between subsequent to assembly of the valve.

* * * * *

UNITED STATES PATENT AND TRADEMARK OFFICE
CERTIFICATE OF CORRECTION

PATENT NO. : 7,892,181 B2  Page 1 of 1
APPLICATION NO. : 11/219319
DATED : February 22, 2011
INVENTOR(S) : Mark A. Christensen et al.

It is certified that error appears in the above-identified patent and that said Letters Patent is hereby corrected as shown below:

In the specification:
COLUMN 2,   LINE 61    change "LAP," to --IAP,--
COLUMN 13,  LINE 50    change "LAP" to --IAP--
COLUMN 15,  LINE 60    change "LAP" to --IAP--
COLUMN 16,  LINE 36    change "LAP" to --IAP--
COLUMN 20,  LINE 41    change "LAP" to --IAP--
COLUMN 21,  LINE 13    change "LAP" to --IAP--

In the claims:
CLAIM 19, COLUMN 25, LINE 20    change "both of" to --both of:--

Signed and Sealed this
Thirty-first Day of May, 2011

David J. Kappos
*Director of the United States Patent and Trademark Office*